United States Patent
Matray et al.

(10) Patent No.: US 9,751,909 B2
(45) Date of Patent: Sep. 5, 2017

(54) SYNTHESIS AND USES OF NUCLEIC ACID COMPOUNDS WITH CONFORMATIONALLY RESTRICTED MONOMERS

(75) Inventors: Tracy J. Matray, Snohomish, WA (US); Iwona M. Maciagiewicz, Oak Park, IL (US); Michael E. Houston, Jr., Sammamish, WA (US)

(73) Assignee: Marina Biotech, Inc., City of industry, CA (US)

( * ) Notice: Subject to any disclaimer, the term of this patent is extended or adjusted under 35 U.S.C. 154(b) by 428 days.

(21) Appl. No.: 14/343,607

(22) PCT Filed: Sep. 7, 2012

(86) PCT No.: PCT/US2012/054308
§ 371 (c)(1),
(2), (4) Date: Nov. 2, 2014

(87) PCT Pub. No.: WO2013/036868
PCT Pub. Date: Mar. 14, 2013

(65) Prior Publication Data
US 2015/0080564 A1 Mar. 19, 2015

Related U.S. Application Data

(60) Provisional application No. 61/532,056, filed on Sep. 7, 2011.

(51) Int. Cl.
| | |
|---|---|
| C07H 21/04 | (2006.01) |
| C07H 19/04 | (2006.01) |
| C07H 19/16 | (2006.01) |
| C07H 19/00 | (2006.01) |
| C07H 19/06 | (2006.01) |
| C07H 23/00 | (2006.01) |
| C07H 19/10 | (2006.01) |
| C12N 15/113 | (2010.01) |

(52) U.S. Cl.
CPC ............ *C07H 19/06* (2013.01); *C07H 19/10* (2013.01); *C07H 19/16* (2013.01); *C07H 23/00* (2013.01); *C12N 15/113* (2013.01)

(58) Field of Classification Search
CPC ...... C12N 15/113; C07H 19/06; C07H 19/10; C07H 23/00
See application file for complete search history.

(56) References Cited

U.S. PATENT DOCUMENTS

| | | | |
|---|---|---|---|
| 5,334,711 A | 8/1994 | Sproat | |
| 5,627,053 A | 5/1997 | Usman | |
| 5,716,824 A | 2/1998 | Beigelman | |
| 5,767,264 A | 6/1998 | Otvos | |
| 5,824,483 A * | 10/1998 | Houston, Jr. | ........... G01N 33/53 435/7.1 |
| 6,001,311 A | 12/1999 | Brennan | |
| 6,083,482 A | 7/2000 | Wang | |
| 6,300,074 B1 | 10/2001 | Gold | |
| 6,403,566 B1 * | 6/2002 | Wang | ..................... C07H 19/04 514/45 |
| 6,833,361 B2 * | 12/2004 | Hong | ..................... C07H 19/04 514/45 |

FOREIGN PATENT DOCUMENTS

| | | |
|---|---|---|
| WO | 8902439 A1 | 3/1989 |
| WO | 9103162 A1 | 3/1991 |
| WO | 9207065 A1 | 4/1992 |
| WO | 9315187 A1 | 8/1993 |
| WO | 9323569 A1 | 11/1993 |
| WO | 9506731 A2 | 3/1995 |
| WO | 9511910 A1 | 5/1995 |
| WO | 9726270 A2 | 7/1997 |
| WO | 9813526 A1 | 4/1998 |
| WO | 9932619 A1 | 7/1999 |
| WO | 9954459 A2 | 10/1999 |

OTHER PUBLICATIONS (R) Wang et al., "Conformationally Locked Nucleosides. Synthesis and Stereochemical Assignments of 2'-C,4'-C-Bridged Bicyclonucleosides," Tetrahedron, 55, 7707-77245 (1999).*
(S) Wang et al., "Conformationally Locked Nucleosides. Synthesis and Hybridization Properties of Oligodeoxynucleotides Containing 2',4'-C-Bridged 2'-Deoxynucleosides," Bioorganic & Medicinal Chemistry Letters, 9, 1147-1150 (1999).*

* cited by examiner

*Primary Examiner* — Lawrence E Crane
(74) *Attorney, Agent, or Firm* — Eckman Law Group

(57) ABSTRACT

Processes for synthesis of conformationally restricted nucleomonomers (CRN) by ozonolysis or oxidation of a 2'-vinyl substituted nucleoside precursor with protected 3'-hydroxyl, 4'-hydroxymethyl and 5'-hydroxyl positions. The CRN nucleomonomers can be used to prepare nucleic acid compounds. CRN nucleomonomers for nucleic acid compounds can be prepared in high yields and in multi-gram scale. The nucleic acid compounds can be of various regulatory classes such as antisense RNA for therapeutic modalities useful for treating or preventing diseases or disorders by up- or down-regulating the expression of genes and other nucleic acid based regulatory systems in a cell.

19 Claims, 2 Drawing Sheets

SEQUENCE LISTING

```
<160> NUMBER OF SEQ ID NOS: 73

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Conformationally restricted nucleomonomer

<400> SEQUENCE: 1
cugccuggca gcccuuucu                                                   19
```

-continued

```
<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (21)..(21)
<223> OTHER INFORMATION: Conformationally restricted nucleomonomer

<400> SEQUENCE: 2
cugccuggca gcccuuucuu u                                                   21

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Conformationally restricted nucleomonomer
<220> FEATURE:
<221> NAME/KEY: modified_base
<222> LOCATION: (22)..(22)
<223> OTHER INFORMATION: Conformationally restricted nucleomonomer

<400> SEQUENCE: 3
ucugccuggc agcccuuucu uu                                                  22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: Conformationally restricted nucleomonomer
<220> FEATURE:
<221> NAME/KEY: modified_base
<222> LOCATION: (21)..(21)
<223> OTHER INFORMATION: Conformationally restricted nucleomonomer

<400> SEQUENCE: 4
cugccuggca gcccuuucuu u                                                   21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Conformationally restricted nucleomonomer

<400> SEQUENCE: 5
cugccuggca gcccuuucuu u                                                   21
```

```
<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (19)..(19)
<223> OTHER INFORMATION: Conformationally restricted nucleomonomer

<400> SEQUENCE: 6
cugccuggca gcccuuucuu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Conformationally restricted nucleomonomer
<220> FEATURE:
<221> NAME/KEY: modified_base
<222> LOCATION: (19)..(19)
<223> OTHER INFORMATION: Conformationally restricted nucleomonomer

<400> SEQUENCE: 7
cugccuggca gcccuuucuu u                                              21

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: Conformationally restricted nucleomonomer
<220> FEATURE:
<221> NAME/KEY: modified_base
<222> LOCATION: (20)..(20)
<223> OTHER INFORMATION: Conformationally restricted nucleomonomer

<400> SEQUENCE: 8
ucugccuggc agcccuuucu uu                                             22

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Conformationally restricted nucleomonomer
<220> FEATURE:
<221> NAME/KEY: modified_base
<222> LOCATION: (19)..(19)
```

<223> OTHER INFORMATION: Conformationally restricted nucleomonomer

<400> SEQUENCE: 9
gaccaccgca ucucuacau                                                   19

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (19)..(19)
<223> OTHER INFORMATION: Conformationally restricted nucleomonomer
<220> FEATURE:
<221> NAME/KEY: modified_base
<222> LOCATION: (21)..(21)
<223> OTHER INFORMATION: Conformationally restricted nucleomonomer

<400> SEQUENCE: 10
gaccaccgca ucucuacauu u                                                21

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
agaaagggcu gccaggcag                                                   19

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
agaaagggcu gccaggcagu u                                                21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
agaaagggcu gccaggcagu u                                                21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 14
agaaagggcu gccaggcagu u                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
agaaagggcu gccaggcagu u                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agaaagggcu gccaggcagu u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agaaagggcu gccaggcagu u                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
agaaagggcu gccaggcagu u                                              21

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auguagagau gcggugguc                                                 19

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
```
auguagagau gcgguggucu u                                             21

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: Conformationally restricted nucleomonomer

<400> SEQUENCE: 21
gagguccuag uggacccacg cagcc                                         25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (25)..(25)
<223> OTHER INFORMATION: Conformationally restricted nucleomonomer

<400> SEQUENCE: 22
agguccuagu ggacccacgc agccg                                         25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Conformationally restricted nucleomonomer
<220> FEATURE:
<221> NAME/KEY: modified_base
<222> LOCATION: (23)..(23)
<223> OTHER INFORMATION: Conformationally restricted nucleomonomer
<220> FEATURE:
<221> NAME/KEY: modified_base
<222> LOCATION: (25)..(25)
<223> OTHER INFORMATION: Conformationally restricted nucleomonomer

<400> SEQUENCE: 23
ccuaguggac ccacgcagcc ggcgg                                         25

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: Conformationally restricted nucleomonomer
<220> FEATURE:

```
<221> NAME/KEY: modified_base
<222> LOCATION: (24)..(25)
<223> OTHER INFORMATION: Conformationally restricted nucleomonomer

<400> SEQUENCE: 24
guggacccac gcagccggcg gcgcu                                              25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: Conformationally restricted nucleomonomer

<400> SEQUENCE: 25
cuccuggagc ugcacaagag gagga                                              25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Conformationally restricted nucleomonomer
<220> FEATURE:
<221> NAME/KEY: modified_base
<222> LOCATION: (24)..(24)
<223> OTHER INFORMATION: Conformationally restricted nucleomonomer

<400> SEQUENCE: 26
ccuggagcug cacaagagga ggaaa                                              25

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (23)..(24)
<223> OTHER INFORMATION: Conformationally restricted nucleomonomer

<400> SEQUENCE: 27
ggcugccagu accugcaccg aaacc                                              25

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: Conformationally restricted nucleomonomer
```

<400> SEQUENCE: 28
gaccucaagc ugggcaaccu uuucc                                    25

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gccuaaaaga gaccuaccuc cggau                                    25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
accuaccucc ggaucaagaa gaaug                                    25

<210> SEQ ID NO 31
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ggcugcgugg guccacuagg accuccg                                  27

<210> SEQ ID NO 32
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cggcugcgug gguccacuag gaccucc                                  27

<210> SEQ ID NO 33
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ccgccggcug cgugggucca cuaggac                                  27

<210> SEQ ID NO 34
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 34
agcgccgccg gcugcguggg uccacua                                              27

<210> SEQ ID NO 35
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uccuccucuu gugcagcucc aggagag                                              27

<210> SEQ ID NO 36
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuuccuccuc uugugcagcu ccaggag                                              27

<210> SEQ ID NO 37
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gguuucggug cagguacugg cagccaa                                              27

<210> SEQ ID NO 38
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggaaaagguu gcccagcuug aggucuc                                              27

<210> SEQ ID NO 39
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: Conformationally restricted nucleomonomer

<400> SEQUENCE: 39
auccggaggu aggucucuuu uaggcaa                                              27

<210> SEQ ID NO 40
<211> LENGTH: 27
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (27)..(27)
<223> OTHER INFORMATION: Conformationally restricted nucleomonomer

<400> SEQUENCE: 40
cauucuucuu gauccggagg uaggucu                                            27

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Conformationally restricted nucleomonomer
<220> FEATURE:
<221> NAME/KEY: modified_base
<222> LOCATION: (21)..(21)
<223> OTHER INFORMATION: 2'-O-methyl nucleotide

<400> SEQUENCE: 41
ccauguggaa aaauaccuau u                                                  21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (21)..(21)
<223> OTHER INFORMATION: Conformationally restricted nucleomonomer

<400> SEQUENCE: 42
cuggauuucu uacagugauu u                                                  21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Conformationally restricted nucleomonomer

<400> SEQUENCE: 43
aguggcugca aaagcucauu u                                                  21

<210> SEQ ID NO 44
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 44
ggcagguccu guuguugguu u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 45
ccagggucuc ccaguacauu u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 46
ucgaguggcu gcaaaagcuu u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (3)..(3)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide
```

```
<400> SEQUENCE: 47
gcggcuguga gcaguacugu u                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (8)..(8)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 48
aggaugacca gcugaucugu u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 49
cgaugcugac uccauguguu u                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer
<220> FEATURE:
<221> NAME/KEY: modified_base
<222> LOCATION: (20)..(21)
<223> OTHER INFORMATION: 2'-O-methyl nucleotide

<400> SEQUENCE: 50
ggcgguuguu uagcucucau u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (20)..(21)
<223> OTHER INFORMATION: 2'-O-methyl nucleotide

<400> SEQUENCE: 51
uagguauuuu uccacauggu u                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 52
aucacuguaa gaaauccagu u                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 53
augagcuuuu gcagccacuu u                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 54
accaacaaca ggaccugccu u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 55
auguacuggg agacccuggu u                                              21

<210> SEQ ID NO 56
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 56
agcuuuugca gccacucgau u                                            21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 57
caguacugcu cacagccgcu u                                            21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 58
cagaucagcu ggucauccuu u                                            21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 59
acacauggag ucagcaucgu u                                            21

<210> SEQ ID NO 60
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-methyl nucleotide

<400> SEQUENCE: 60
ugagagcuaa acaaccgccu u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: Conformationally restricted nucleomonomer

<400> SEQUENCE: 61
ggacauucag aacaagaaau u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Conformationally restricted nucleomonomer

<400> SEQUENCE: 62
acagaguccc ucaaacagau u                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Conformationally restricted nucleomonomer

<400> SEQUENCE: 63
caucacacug aauaccaauu u                                              21

<210> SEQ ID NO 64
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: Conformationally restricted nucleomonomer

<400> SEQUENCE: 64
aagggaaucu uauauuugau ccaaa                                            25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Conformationally restricted nucleomonomer

<400> SEQUENCE: 65
acagaguccc ucaaacagac augac                                            25

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Conformationally restricted nucleomonomer
<220> FEATURE:
<221> NAME/KEY: modified_base
<222> LOCATION: (25)..(25)
<223> OTHER INFORMATION: Conformationally restricted nucleomonomer

<400> SEQUENCE: 66
gucucaaaag guuuacuaau auucg                                            25

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuucuuguuc ugaauguccu u                                                21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ucuguuugag ggacucuguu u                                                21

<210> SEQ ID NO 69
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
auugguauuc agugugaugu u                                                   21

<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uuuggaucaa auauaagauu cccuucu                                             27

<210> SEQ ID NO 71
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gucaugucug uuugagggac ucuguga                                             27

<210> SEQ ID NO 72
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cgaauauuag uaaaccuuuu gagacug                                             27

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: Phosphorothioate linkage between nucleotides
<220> FEATURE:
<221> NAME/KEY: modified_base
<222> LOCATION: (1)..(1)
<223> OTHER INFORMATION: Conformationally restricted 5'-methyl
      nucleomonomer
<220> FEATURE:
<221> NAME/KEY: modified_base
<222> LOCATION: (2)..(3)
<223> OTHER INFORMATION: deoxy-nucleotide
<220> FEATURE:
<221> NAME/KEY: modified_base
<222> LOCATION: (4)..(5)
<223> OTHER INFORMATION: Conformationally restricted nucleomonomer
<220> FEATURE:
<221> NAME/KEY: modified_base
<222> LOCATION: (6)..(6)
<223> OTHER INFORMATION: deoxy-nucleotide
```

```
<220> FEATURE:
<221> NAME/KEY: modified_base
<222> LOCATION: (7)..(7)
<223> OTHER INFORMATION: Conformationally restricted nucleomonomer
<220> FEATURE:
<221> NAME/KEY: modified_base
<222> LOCATION: (8)..(8)
<223> OTHER INFORMATION: Conformationally restricted 5'-methyl
      nucleomonomer
<220> FEATURE:
<221> NAME/KEY: modified_base
<222> LOCATION: (9)..(9)
<223> OTHER INFORMATION: deoxy-nucleotide
<220> FEATURE:
<221> NAME/KEY: modified_base
<222> LOCATION: (10)..(10)
<223> OTHER INFORMATION: Conformationally restricted 5'-methyl
      nucleomonomer
<220> FEATURE:
<221> NAME/KEY: modified_base
<222> LOCATION: (11)..(13)
<223> OTHER INFORMATION: deoxy-nucleotide
<220> FEATURE:
<221> NAME/KEY: modified_base
<222> LOCATION: (14)..(15)
<223> OTHER INFORMATION: Conformationally restricted 5'-methyl
      nucleomonomer
<220> FEATURE:
<221> NAME/KEY: modified_base
<222> LOCATION: (16)..(16)
<223> OTHER INFORMATION: deoxy-nucleotide

<400> SEQUENCE: 73
ccattgtcac actcca                                              16
```

SYNTHESIS AND USES OF NUCLEIC ACID COMPOUNDS WITH CONFORMATIONALLY RESTRICTED MONOMERS

CROSS REFERENCE TO RELATED APPLICATIONS

This application is the US National Stage of PCT/US2012/054308, filed Sep. 7, 2012, and claims priority to U.S. Provisional Patent Application No. 61/532,056, filed Sep. 7, 2011.

SEQUENCE LISTING

This application includes a Sequence Listing submitted electronically herewith as an ASCII file created on Aug. 11, 2014, named MAR240US_SL.txt, which is 25,477 bytes in size, and is hereby incorporated by reference in its entirety.

TECHNICAL FIELD

This invention relates to the synthesis and uses of nucleic acid compounds for treating disease by regulating the expression of genes and other cell regulatory systems dependent upon a nucleic acid in a cell. More specifically, this disclosure relates to the synthesis of a range of conformationally restricted nucleomonomers (CRN) which can be used to prepare single-stranded and multi-stranded nucleic acid compounds.

BACKGROUND

The identification and evaluation of microRNAs is one of the fastest growing fields in biology and medicine. Micro-RNAs are considered to be key elements in maintaining normal cell physiology as microRNAs appear to be central regulators of gene expression that are critical for intra- and extra-cellular events. Thus, either the loss of specific micro-RNAs or the overexpression of specific microRNAs can lead to abnormal cell processes that are the underlying basis for disease. Inhibition of an aberrant microRNA with an antagonist, or the supplementation with a microRNA mimetic, can restore the balance between cellular communication pathways. Therapeutics approaches using nucleic acid compounds containing a CRN can directly and efficiently alter the function of microRNAs.

Nucleic acid compounds containing a conformationally restricted nucleomonomer or CRN can be used as micro-RNA antagonists. The therapeutic benefit of inhibiting a specific microRNA is the de-repression of downstream targets controlled by the microRNA. De-repression allows the downstream targets to express proteins which the micro-RNA typically down regulates. Thus, microRNA inhibition is one of the few therapeutic approaches that permits "upregulation" of specific gene targets.

RNA interference or RNAi refers to the cellular process of sequence specific, post-transcriptional gene silencing mediated by small inhibitory nucleic acid molecules. An RNAi active molecule can be a double-stranded RNA or dsRNA that has a portion that is homologous to a portion of a targeted messenger RNA. A long dsRNA may be processed by Dicer enzyme into a short interfering RNA or siRNA having from 21 to 23 nucleotides with double-stranded regions of about 19 base pairs and a two nucleotide, generally, overhang at each 3'-end. An siRNA can interact with an RNA-induced silencing complex or RISC complex which cleaves the passenger or sense strand of the siRNA. The guide or antisense strand of the siRNA can bind a complementary target mRNA, which is then cleaved by the RISC to cause gene silencing.

Nucleic acid compounds containing a CRN can be used to increase the affinity of a single-stranded oligonucleotide to its intended target, whether it is a messenger RNA or microRNA.

Nucleic acid compounds containing a CRN can be used to silence gene targets through either RNA interference or translational blocking, or via a microRNA mimetic. They can be used to up-regulate gene targets via a microRNA antagonist.

What is needed are efficient methods for preparing nucleomonomers for nucleic acid compounds in high yield at multi-gram scale for therapeutic modalities useful for treating or preventing diseases or disorders by up- or down-regulating the expression of genes and other nucleic acid based regulatory systems in a cell.

A need therefore exists for methods for preparing nucleomonomers for nucleic acid compounds having enhanced stability that are useful in various therapeutic modalities involving microRNA, siRNA, and/or antisense RNA.

BRIEF SUMMARY

Embodiments of this invention include:
A method for making a compound having Formula V

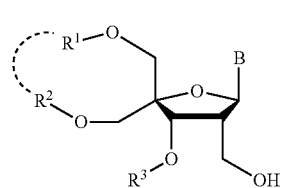

Formula V wherein $R^1$ is a substituent protecting group, $R^2$ is a substituent protecting group, one or both of $R^1$ and $R^2$ are bulky substituent protecting groups, $R^1$ and $R^2$ are optionally linked, $R^3$ is a protecting group, and B is a nucleobase or nucleobase analog, the method comprising providing a compound having Formula II,

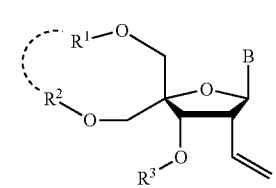

Formula II transforming the compound having Formula II by ozonolysis or oxidation, and isolating the compound having Formula V. B can be uridine or 5-methyluridine. $R^1$ and $R^2$ can be a 1,1,3,3-tetraalkyldisiloxane-1,3-diyl group. $R^1$ and $R^2$ can be a 1,1,3,3-tetraisopropyldisiloxane-1,3-diyl group. $R^3$ may be benzyl.

The yield of the compound having Formula V by ozonolysis can be at least 50% at a scale of at least 5 grams of the compound having Formula V. The yield of the compound having Formula V by ozonolysis can be at least 50% at a scale of at least 10 grams of the compound having Formula V. The yield of the compound having Formula V ozonolysis may be at least 70% at a scale of at least 10 grams of the compound having Formula V. The yield of the compound having Formula V ozonolysis can be at least 80% at a scale of at least 10 grams of the compound having Formula V.

The method above, further comprising transforming the compound having Formula V to a conformationally restricted nucleomonomer CRN having Formula VI, Formula VI

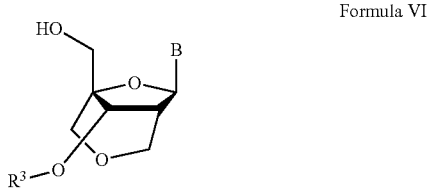

by protecting the 5'-hydroxyl group, and substituting $R^3$ with a phosphoramidite. The 5'-hydroxyl group can be protected with a DMTr group. B may be transformed to a cytidinyl, uridinyl, or thymidinyl group. The conformationally restricted nucleomonomer can be a pyrimidine CRN. The pyrimidine CRN can be transformed to a purine CRN by transglycosidation of the pyrimidine CRN. The CRN can be used to make a nucleic acid compound. The nucleic acid compound may be a single stranded oligonucleotide or a double-stranded oligonucleotide. The nucleic acid compound can be a microRNA, an antimir, an antagomir, a microRNA mimetic, a microRNA precursor, an RNA, an siRNA, a DNA, an RNA and DNA, a usiRNA, an mdRNA, a short hairpin RNA or shRNA, or an antisense oligonucleotide. This disclosure describes methods for making a purine CRN by synthesizing a bicyclic sugar and reacting the bicyclic sugar with silylated purine. The bicyclic sugar may have Formula VI, wherein B is replaced by an alkoxy group.

A CRN having the structure

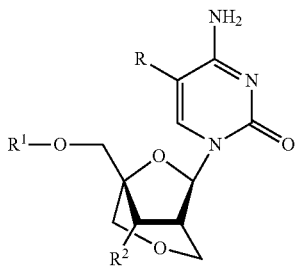

wherein R is methyl, $R^1$ is independently H, alkyl, or a protecting group, and $R^2$ is independently H, alkyl, a protecting group, or a phosphoramidite group.

A CRN having the structure

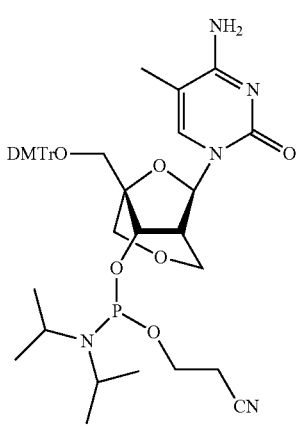

A nucleic acid compound comprising the CRN above. The nucleic acid compound may be a single stranded oligonucleotide or a double-stranded oligonucleotide.

DETAILED DESCRIPTION

Figure 1:
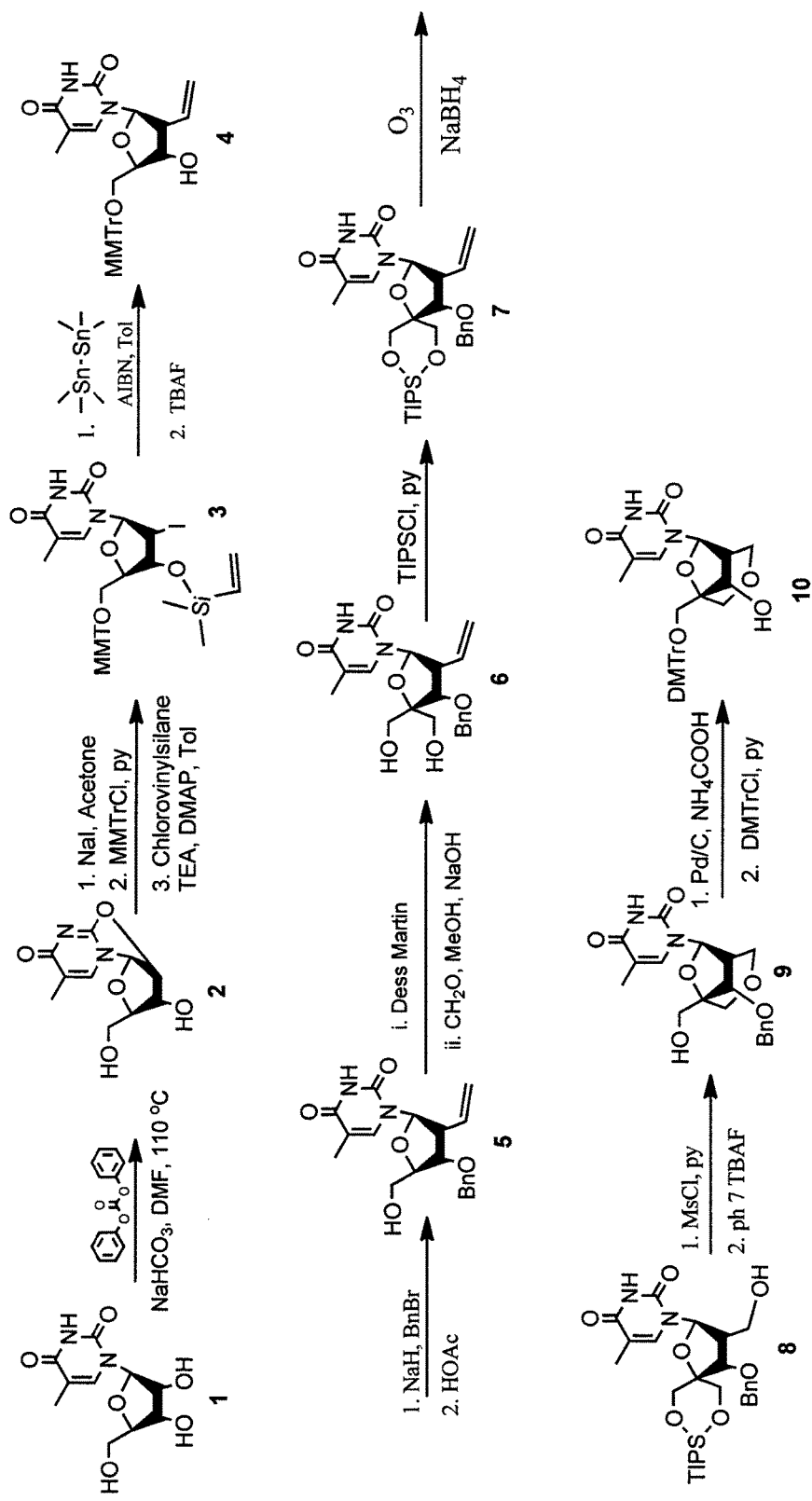
FIG. 1 shows embodiments of methods for making a conformationally restricted nucleomonomer or CRN of this disclosure.

This invention relates to the synthesis and uses of nucleic acid compounds containing one or more conformationally restricted nucleomonomers. A conformationally restricted nucleomonomer or CRN is a molecule having a bridge connecting the C2' and C4' ribose carbons of a ribonucleic acid. Substitution of a CRN within an RNA- or DNA-based oligonucleotide can increase hybridization affinity and enhance resistance to nuclease degradation. CRN technology provides a direct means of developing highly potent and specific nucleic acid-based therapeutics to target messenger RNAs or microRNAs. These targets represent disease pathways that are typically "undruggable" or "difficult to target" by small molecule or monoclonal antibodies, and are appropriate for disease areas with significant unmet needs, such as inflammation, metabolic disease, and cancers.

This disclosure relates generally to nucleic acid compounds for use in treating disease by gene silencing or modulating the function of a cell regulatory system dependent upon a nucleic acid in a cell.

Conformationally Restricted Nucleomonomers

In some aspects, a nucleic acid compound of this disclosure can contain one or more conformationally restricted nucleomonomers which advantageously enhance the stability of the compound in various therapeutic modalities.

Synthesis of some conformationally restricted nucleomonomers is described in U.S. Pat. Nos. 6,833,361; 6,403,566 and 6,083,482.

In some embodiments, the conformationally restricted nucleomonomer is Monomer R and has the following formula:

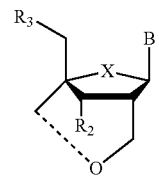

where X is independently for each occurrence selected from O, S, $CH_2$, C=O, C=S, $C=CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog. In a nucleic acid compound incorporating a CRN based on Monomer R, $R_2$ and $R_3$ can be phosphodiester linkages of the nucleic acid compound.

In certain embodiments, the conformationally restricted nucleomonomer is Monomer S and has the following formula:

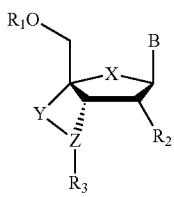

where X is independently for each occurrence selected from O, S, $CH_2$, C=O, C=S, $C=CH_2$, CHF, $CF_2$; Z is O; Y is $CH_2$; $R_2$ is independently for each occurrence selected from hydrogen, F, OH, or $OCH_3$; $R_1$ and $R_3$ are independently for each occurrence selected from hydrogen, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR. In a nucleic acid compound incorporating a CRN based on Monomer S, $R_1$ and $R_3$ can be phosphodiester linkages of the nucleic acid compound.

In certain embodiments, a nucleic acid compound may contain any number of CRNs. A nucleic acid compound of this disclosure may contain one or more Monomer R, and one or more Monomer S.

In some embodiments, B represents a nucleobase or nucleobase analog independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynylcytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and any existing deoxy analogs of the foregoing.

In some embodiments, B represents a nucleobase or nucleobase analog independently selected from adenine, cytosine, guanine, uracil, and any existing deoxy analogs of the foregoing.

In some embodiments, a nucleic acid compound may contain one or more CRNs and one or more hydroxymethyl substituted nucleomonomers or UNAs. Some structures and methods for synthesis of hydroxymethyl substituted nucleomonomers and hydroxymethyl substituted nucleic acid compounds may be found in PCT International Application PCT/US2008/064417.

In another aspect, a nucleic acid compound of this disclosure may contain a nucleotide analogue selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers, and INA monomers.

Synthesis of Conformationally Restricted Nucleomonomers

A pyrimidine analogue of a conformationally restricted nucleomonomer can be synthesized from a uridine or 5-substituted uridine nucleoside. To synthesize the CRN or bicyclic nucleoside, carbon atoms can be added at the 2' and 4' positions. The carbon atom substituents at the 2' and 4' positions can be used to form a 2'-4' bridge in the nucleoside, thereby forming the bicyclic CRN.

Sukeda et al. demonstrated one way to add a carbon atom at the 2' position by intramolecular transfer of a vinyl group from a siloxyl protecting group at the 3' position. See Sukeda et al., J. Org. Chem. Vol. 65, 8988-8996, 2000. The vinyl group was transferred to provide the (R)-2'-vinyl substituted ribo-configured nucleoside stereoisomer.

In the methods of this disclosure, starting from a 2,2'-anhydrouridine intermediate of either a uridine or 5-methyluridine ribonucleoside, the 5'-hydroxyl group can be protected with a monomethoxy trityl group (MMT). Then, nucleophilic ring opening with sodium iodide and tosic acid affords a 2'-deoxy-2'-iodo-3'-O-dimethylvinylsilyl-5'-MMT-O-pyrimidine ribonucleoside. A monomethoxy trityl group is preferred over a dimethoxy trityl group to protect the 5'-hydroxyl group because the monomethoxy trityl group is more stable in the subsequent vinyl transfer reaction. Upon completion of a radical-initiated vinyl transfer reaction, residual silane can be removed using tetrabutylammonium fluoride (TBAF). A single purification step can be used, and the procedure is scalable to 50 gram quantities or more of product 2'-deoxy-2'-vinyl-5'-MMT-O-pyrimidine ribonucleoside.

For the 3' position, the 3' position can be protected with a benzyl group, the MMT protecting group can be removed, and the 5' position can be oxidized with Dess-Martin periodinane to introduce a 4'-hydroxymethyl group. The resulting diol compound having Formula I

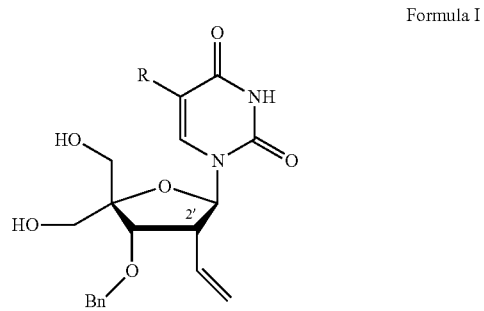

Formula I contains the appropriate 2' and 4' carbon atom substituents to prepare a range of CRNs and CRN-containing molecules. The diol compound Formula I can be prepared by various methods known in the art. In certain embodiments, R is H or methyl.

What is not known in the art is a robust route from a diol compound having Formula I to a CRN nucleomonomer with high yield and in multi-gram scale.

The 2'-vinyl substituent of a diol having Formula I must be transformed to a reactive group that can form a covalent bridge with a 4' substituent. One way to reach the CRN is to transform the 2'-vinyl substituent to a 2'-hydroxymethyl substituent. In performing this transformation, a significant problem is to achieve high yield of the 2'-hydroxymethyl substituent at multi-gram scale of nucleomonomer.

For example, addition of mesylate groups to the 4'-hydroxymethyl and 5'-hydroxyl groups of the diol Formula I is insufficient protection to withstand treating the diol Formula I with, for example, osmium tetroxide to transform the 2'-vinyl substituent to a 2'-hydroxymethyl substituent. In general, only low yields could be obtained.

Further, the 2'-vinyl substituent of a diol compound having Formula I could not be sufficiently transformed to a 2'-hydroxymethyl substituent by ozonolysis. In practice, low yields could only be obtained at small scale of less than a gram, making the method impractical. Without wishing to be bound by any particular theory, it may be that the 3'-benzyl protecting group exhibits reactivity under ozonolysis, among other things.

In some aspects, this invention provides a successful route from the diol compound of Formula I to a CRN nucleomonomer with high yields and in multi-gram scale.

It has been found that an unexpectedly advantageous stable intermediate for ozonolysis and other routes of transformation can be a protected compound having Formula II

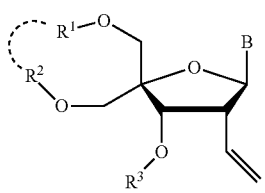

Formula II where the 5'-hydroxyl is protected with bulky substituent $R^1$, the 4'-hydroxymethyl is protected with bulky substituent $R^2$, the 3'-hydroxyl is protected with substituent $R^3$, and B is a nucleobase or nucleobase analog. Substituents $R^1$ and $R^2$ are optionally linked as shown by the dotted line.

In some embodiments, one of substituents $R^1$ and $R^2$ is a bulky substituent.

In some embodiments, an advantageously stable intermediate for ozonolysis and other routes of transformation can be the protected compound having Formula III

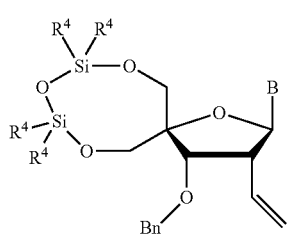

Formula III where the 5'-hydroxyl and 4'-hydroxymethyl are protected with a 1,1,3,3-tetraalkyldisiloxane-1,3-diyl group, the $R^4$ are alkyl groups, Bn is benzyl, and B is a nucleobase or nucleobase analog. In certain embodiments, $R^4$ is isopropyl.

In some embodiments, the nucleobase is a uridine or 5-methyluridine, and a protected compound may have Formula IV

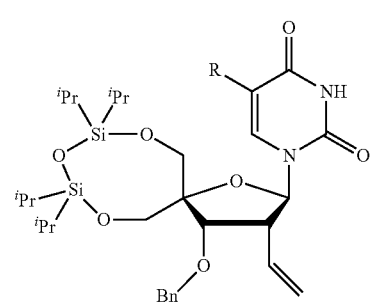

Formula IV where R is hydrogen or methyl, $^iPr$ is isopropyl, and the 5'-hydroxyl and 4'-hydroxymethyl are protected with a 1,1,3,3-tetraisopropyldisiloxane-1,3-diyl group (TIPDS or TIPS).

Examples of bulky substituents for positions $R^1$ and $R^2$ include trimethylsilyl (TMS), tert-butyldimethylsilyl (TBDMS), tri-iso-propylsilyloxymethyl (TOM).

Examples of bulky substituents for positions $R^1$ and $R^2$ include dimethoxytrityl (DMT) (bis-(4-methoxyphenyl)phenylmethyl).

A protected compound having Formula II, III or IV can be advantageously stable with respect to ozonolysis and other routes of transformation of the 2'-vinyl substituent. Upon ozonolysis, the compound of formula IV is transformed to a compound having Formula V

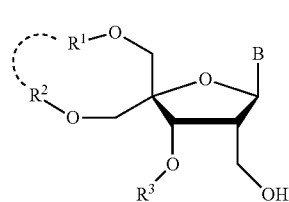

Formula V

The unexpectedly advantageous stability of a protected compound having Formula II, III or IV can include reduced sensitivity of the 3'-benzyl protecting group to ozonolysis, among other things. Initial yields of transformation of the 2'-vinyl substituent by ozonolysis can be 50% or greater, along with 40% recovery of the 2'-vinyl form that could be further oxidized giving yields up to 90%.

By using a protected compound having Formula II, III or IV as a starting point, the transformation of the 2'-vinyl substituent can be achieved in high yield at high scale to afford the synthesis of a CRN in high yield at high scale.

A protected compound having Formula II, III or IV can be transformed to a CRN by: (a) ozonolysis of the 2'-vinyl substituent to a 2'-hydroxymethyl substituent, (b) acylating the 2'-hydroxymethyl substituent to give a fully-protected nucleoside, (c) regenerating the diol form by removing the TIPDS group with buffered tetrabutylammonium fluoride, (d) mesylating the 4'-hydroxymethyl substituent and 5'-hydroxyl group of the regenerated diol form, (e) deacylating the 2'-position, and (f) condensing the α-4'-mesyl-O-substituent with the 2'-hydroxymethyl substituent to form the bicyclic structure. At this point, the partially protected bicyclic nucleoside,

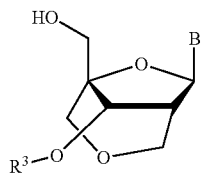

Formula VI can be phosphoramidited with additional steps.

For example, in some embodiments, a phosphoramidite group can be added by: (f1) replacing the 3'-benzyl group with hydrogen, (g1) protecting the remaining β-4'-hydroxymethyl substituent with a group suitable for phosphoramidite chemistry, for example, a 4,4'-dimethoxytrityl (DMTr) group, and (h1) adding a 3'-phosphoramidite group to achieve the CRN phosphoramidite,

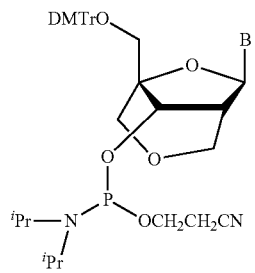

Formula VII

In further embodiments, a phosphoramidite group can be added by: (f2) replacing the 3'-benzyl group with hydrogen, (g2) adding a 3'-triethylsilyl group, and (h2) converting the 4'-acyl to a benzylamino group or benzylcytidine. At this point, the partially protected bicyclic nucleoside can be phosphoramidited with additional steps. By this route, each of the thymidine, cytidine and uridine forms of the 3'-phosphoramidited CRN can be prepared.

In an alternative embodiment, a protected compound having Formula II, III or IV can be transformed to a CRN by: (a) ozonolysis of the 2'-vinyl substituent to a 2'-hydroxymethyl substituent, (b) mesylating the 2'-hydroxymethyl substituent, (c) regenerating the diol form by removing the TIPDS group with buffered tetrabutylammonium fluoride, and (d) condensing the α-4'-hydroxymethyl-substituent with the 2'-mesyl-O substituent to form the bicyclic structure. At this point, the partially protected bicyclic nucleoside,

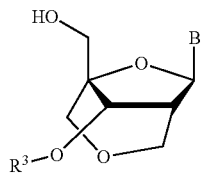

Formula VI can be phosphoramidited with additional steps.

In some embodiments, the following reactions can be done,

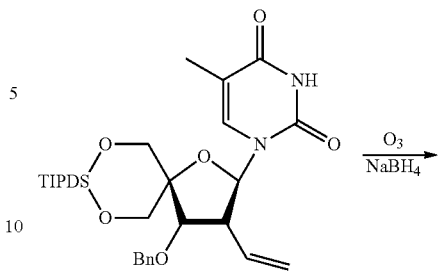

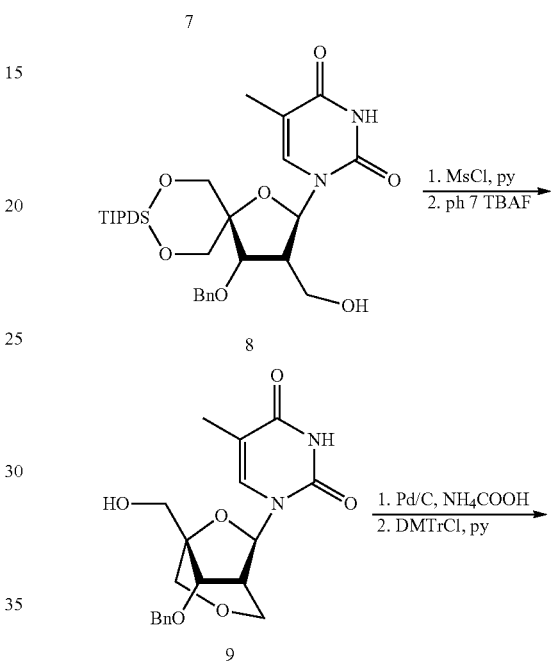

In further embodiments, the following reactions can be done,

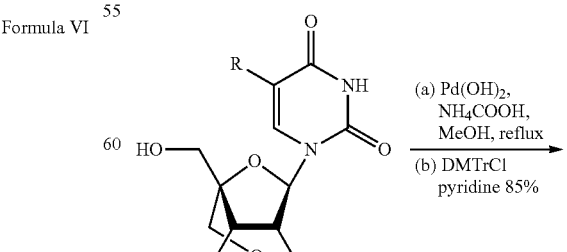

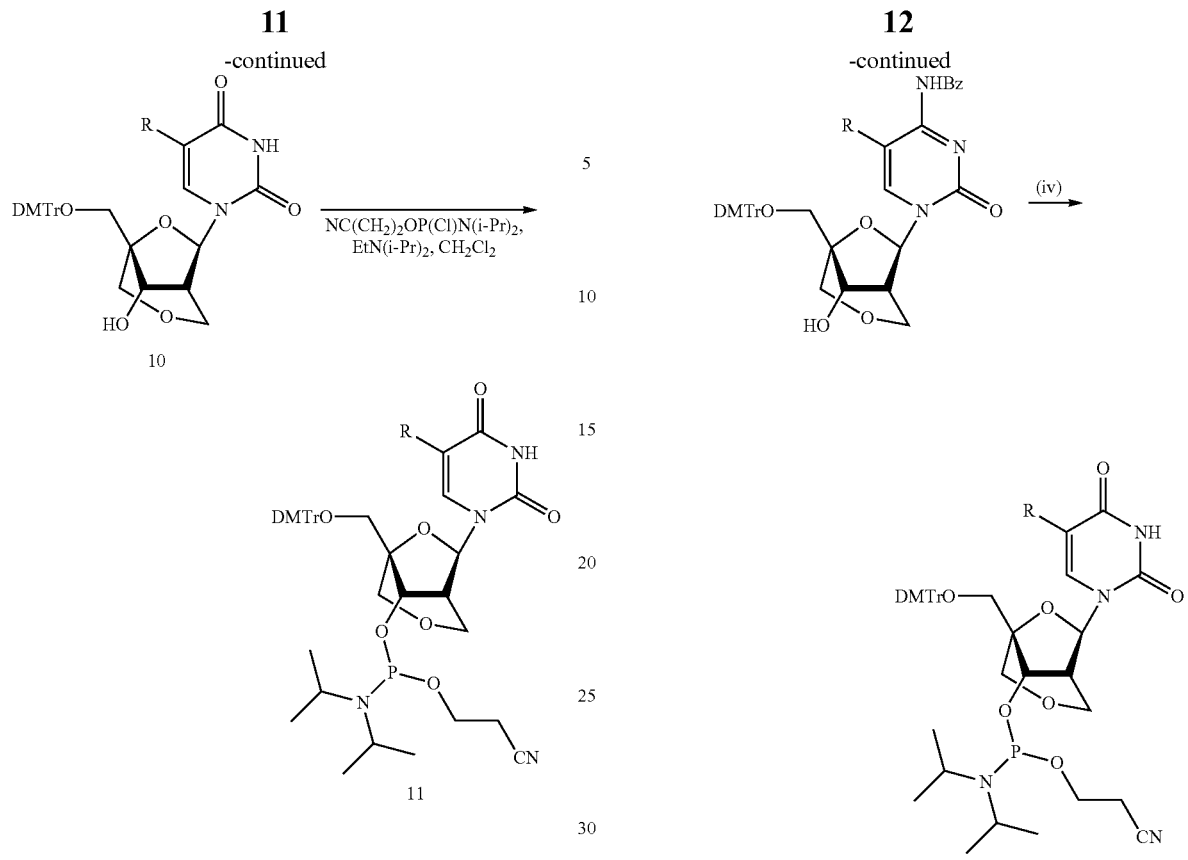
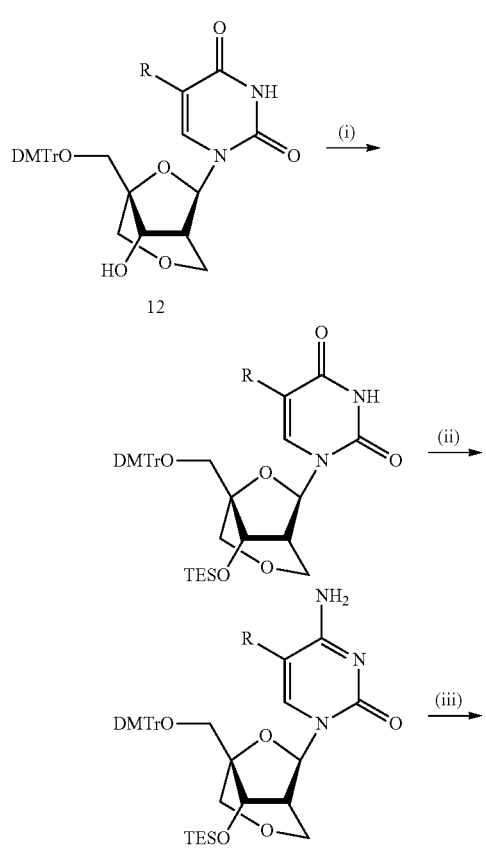

In additional embodiments, the following reactions can be done, (i) TESCl, imidazole, DMR, rt;
(ii) (a) 1,2,4-Triazole, TEA, POCl₃, ACN; (b) NH₄OH, Dioxane;
(iii) (a) benzoic anhydride, DMF, rt; (b) TBAF, THF, rt;
(iv) NC(CH₂)₂OP(Cl)N(i-Pr)₂, EtN(i-Pr)₂, CH₂Cl₂ where TES is triethylsilyl.

FIG. 1 shows embodiments of methods for making a conformationally restricted nucleomonomer or CRN of this disclosure.

Figure 2:
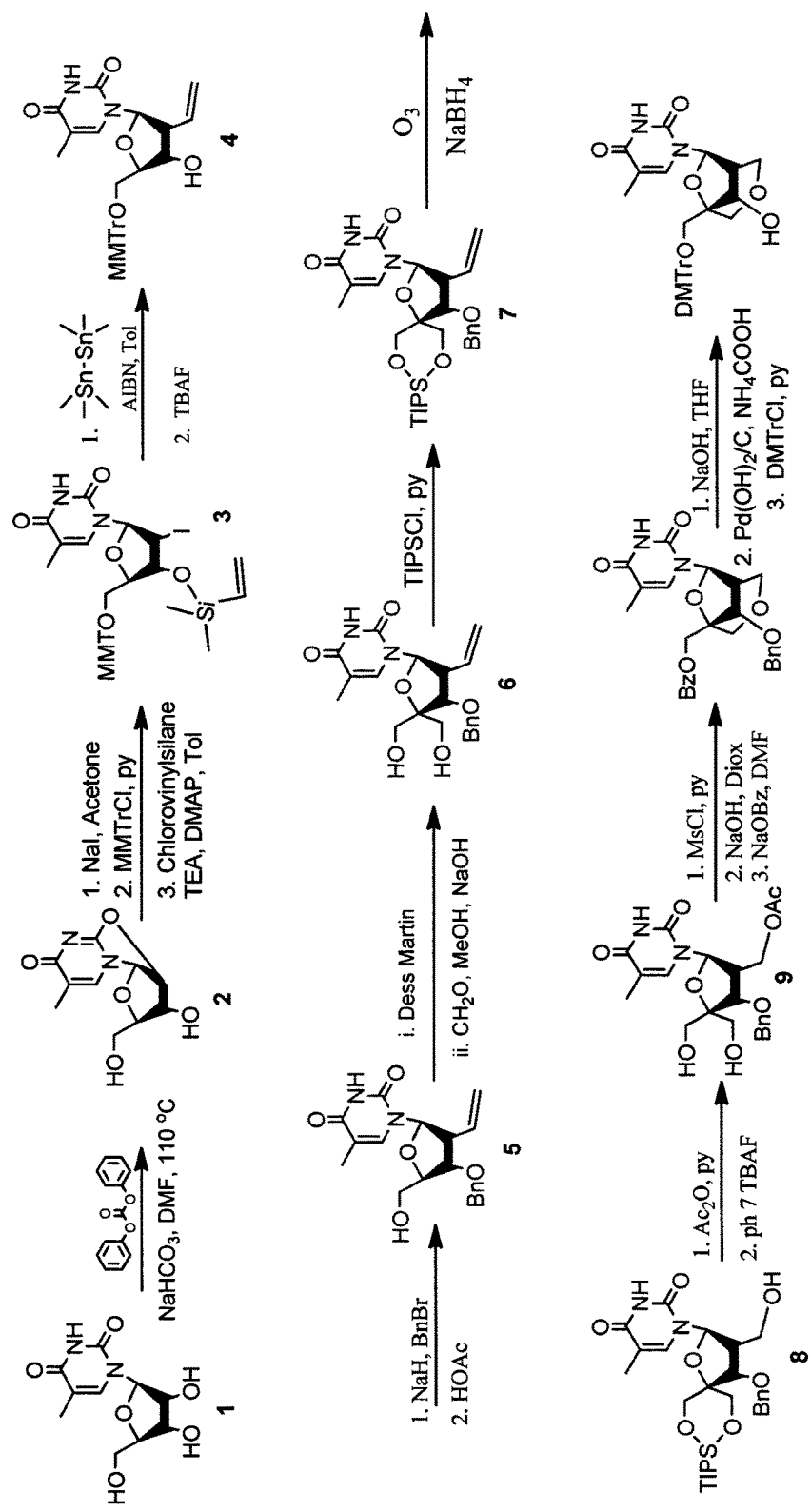
FIG. 2 shows embodiments of methods for making a conformationally restricted nucleomonomer or CRN of this disclosure.

FIG. 2 shows embodiments of methods for making a conformationally restricted nucleomonomer or CRN of this disclosure.

In further embodiments, purine ribonucleosides can be accessed by transglycosidation of the pyrimidine CRN.

In additional embodiments, purine CRN nucleomonomers can be prepared by synthesizing the bicyclic sugar and reacting with silylated purine.

Methods to prepare various organic groups and protective groups are known in the art and their use and modification is generally within the ability of one of skill in the art. See, e.g., Stanley R. Sandler and Wolf Karo, Organic Functional Group Preparations (1989); Greg T. Hermanson, Bioconjugate Techniques (1996); Leroy G. Wade, Compendium Of Organic Synthetic Methods (1980); examples of protective groups are found in T. W. Greene and P. G. M. Wuts, Protective Groups In Organic Synthesis (3rd ed. 1991). See, e.g., Helmut Vorbrüggen, Handbook of Nucleoside Synthesis (2001).

Conformationally Restricted Nucleomonomers

In some aspects, this disclosure provides a range of CRN compounds.

In some embodiments, a CRN compound has the structure

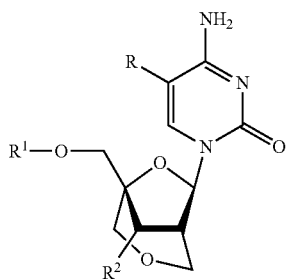

where R is methyl, $R^1$ is independently H, alkyl, or a protecting group, and $R^2$ is independently H, alkyl, a protecting group, or a phosphoramidite group.

The CRN compounds of this disclosure can be made by the methods disclosed herein, in view of techniques in the art.

In some embodiments, a CRN compound of this disclosure is a phosphoramidite 5-methylcytidine CRN,

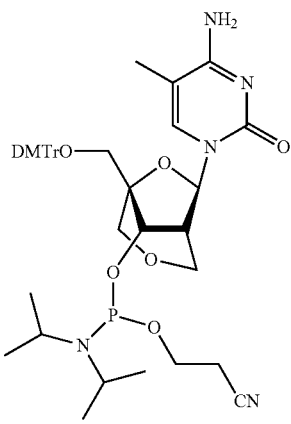

Nucleic Acid Compounds Containing CRN Nucleomonomers

A nucleic acid compound of this disclosure which contains one or more CRNs may be a microRNA, an antimir, an antagomir, a microRNA mimetic, or a microRNA precursor or pre-microRNA.

In some embodiments, a nucleic acid compound of this disclosure may be a single stranded antisense molecule that can be used for targeting a microRNA.

In further embodiments, a nucleic acid compound of this disclosure may be a microRNA mimicking molecule, which is an RNA complex.

In certain embodiments, a nucleic acid compound of this disclosure may be a large intervening noncoding RNA (lincRNA) or a Piwi-interacting RNA (piRNA).

A nucleic acid compound of this disclosure which contains one or more CRNs may be an RNA, a DNA, an RNA and DNA, a usiRNA, an siRNA, an mdRNA, a short hairpin RNA or shRNA, or an antisense oligonucleotide.

In one aspect, the present disclosure provides a nucleic acid compound comprising a first strand and a second strand complementary to the first strand, wherein the first strand and the second strand can anneal to form a double-stranded region, and wherein the double-stranded region comprises one or more mismatches, and wherein one or more of the nucleomonomers of the first strand or the second strand is a conformationally restricted nucleomonomer.

In some embodiments, a nucleic acid compound of this disclosure may have two strands that together constitute an RNA duplex. An RNA duplex can be composed of an antisense strand, also called a guide strand or first strand, and a passenger strand, also called a sense strand or second strand.

In further embodiments, a nucleic acid compound of this disclosure may be a single stranded RNA molecule, for example an antisense RNA, or a functional RNA (fRNA), or a non-coding RNA (ncRNA), or a small temporal RNA (stRNA), or a microRNA (miRNA), or a small nuclear RNA (snRNA), or a short interfering RNA (siRNA), or a small nucleolar RNA (snRNA), or a ribosomal RNA (rRNA), or a transfer RNA (tRNA), or a precursor RNA of any of the forgoing.

In addition, as used herein, the term dsRNA is meant to be equivalent to other terms used to describe nucleic acid molecules that are capable of mediating sequence specific RNAi, for example, meroduplex RNA (mdRNA), nicked dsRNA (ndsRNA), gapped dsRNA (gdsRNA), short interfering nucleic acid (siNA), siRNA, micro-RNA (miRNA), short hairpin RNA (shRNA), short interfering oligonucleotide, short interfering substituted oligonucleotide, short interfering modified oligonucleotide, chemically-modified dsRNA, or post-transcriptional gene silencing RNA (ptgsRNA).

In certain embodiments, a nucleic acid compound of this disclosure may have from 1% to 75% of the nucleomonomers of a strand of the nucleic acid compound being conformationally restricted nucleomonomers.

A nucleic acid compound may have a strand that is from 8 to 60 nucleomonomers in length. A nucleic acid compound may have a strand that is from 10 to 40 nucleomonomers in length.

A nucleic acid compound may have a double-stranded region of from 10 to 23 base pairs, or from 12 to 21 base pairs, or from 14 to 21 base pairs, or from 15 to 21 base pairs, or from 16 to 21 base pairs.

In some embodiments, a nucleic acid compound may be a RISC activator in which the first strand has about 15 nucleotides to about 25 nucleotides, or a Dicer substrate in which the first strand has from about 26 nucleotides to about 40 nucleotides.

In certain embodiments, a nucleic acid compound may contain one or more 5-methyluridine (ribothymidine), one or more 2-thioribothymidine, or one or more universal-binding nucleotides, or one or more G clamps. Examples of a universal-binding nucleotide include C-phenyl, C-naphthyl, inosine, azole carboxamide, 1-β-D-ribofuranosyl-4-nitroindole, 1-β-D-ribofuranosyl-5-nitroindole, 1-β-D-ribofuranosyl-6-nitroindole, and 1-β-D-ribofuranosyl-3-nitropyrrole.

In further embodiments, a nucleic acid compound may further contain a terminal cap substituent on one or both ends of one or more of the first strand, second strand, or third strand. Examples of a terminal cap include alkyl, abasic, deoxy abasic, glyceryl, dinucleotide, acyclic nucleotide, or inverted deoxynucleotide moieties.

A nucleic acid compound may further contain one or more modified internucleoside linkages, such as a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, or boranophosphate linkage.

In a nucleic acid compound, the 5'-terminus of the sense strand, the antisense strand, or both strands may be a hydroxyl or a phosphate.

A nucleic acid compound may be a bifunctional nucleic acid compound having two blunt-ends.

A nucleic acid compound may contain one or more hydroxymethyl substituted nucleomonomers and one or more conformationally restricted nucleomonomers.

In a nucleic acid compound, the first and second strands may be joined by a non-pairing region of nucleomonomers.

A dsRNA molecule may be a meroduplex RNA or mdRNA having three or more strands. For example, an mdRNA may have an 'A' (first or antisense) strand, 'S1' (second) strand, and 'S2' (third) strand in which the 'S1' and 'S2' strands are complementary to, and form base pairs (bp) with non-overlapping regions of the 'A' strand (e.g., an mdRNA can have the form of A:S1S2). The S1, S2, or more strands together essentially comprise a sense strand to the 'A' strand. The double-stranded region formed by the annealing of the 'S1' and 'A' strands is distinct from and non-overlapping with the double-stranded region formed by the annealing of the 'S2' and 'A' strands. An mdRNA molecule is a "gapped" molecule, meaning a "gap" ranging from 0 nucleotides up to about 10 nucleotides. In some embodiments, the A:S1 duplex is separated from the A:S2 duplex by a gap resulting from at least one unpaired nucleotide (up to about 10 unpaired nucleotides) in the 'A' strand that is positioned between the A:S1 duplex and the A:S2 duplex and that is distinct from any one or more unpaired nucleotide at the 3'-end of one or more of the 'A', 'S1', or 'S2' strands. In some embodiments, the A:S1 duplex is separated from the A:B2 duplex by a gap of zero nucleotides (i.e., a nick in which only a phosphodiester bond between two nucleotides is broken or missing in the polynucleotide molecule) between the A:S1 duplex and the A:S2 duplex—which can also be referred to as nicked dsRNA (ndsRNA). For example, A:S1S2 may be comprised of a dsRNA having at least two double-stranded regions that combined total about 14 base pairs to about 40 base pairs and the double-stranded regions are separated by a gap of about 0 to about 10 nucleotides, optionally having blunt ends, or A:S1S2 may comprise a dsRNA having at least two double-stranded regions separated by a gap of up to 10 nucleotides wherein at least one of the double-stranded regions comprises between about 5 base pairs and 13 base pairs.

Synthesis of Nucleic Acid Molecules

Nucleic acid molecules can be recombinantly produced, chemically synthesized, or a combination thereof. Oligonucleotides (e.g., certain modified oligonucleotides or portions of oligonucleotides lacking ribonucleotides) can be synthesized using protocols known in the art, for example as described in Caruthers et al., *Methods in Enzymol*. 211:3-19, 1992; Thompson et al., PCT Publication No. WO 99/54459, Wincott et al., *Nucleic Acids Res*. 23:2677-2684, 1995; Wincott et al., *Methods Mol. Bio*. 74:59, 1997; Brennan et al., *Biotechnol Bioeng*. 61:33-45, 1998; and Brennan, U.S. Pat. No. 6,001,311. Synthesis of RNA, including certain dsRNA molecules and analogs thereof of this disclosure, can be made using the procedure as described in Usman et al., *J. Am. Chem. Soc*. 109:7845, 1987; Scaringe et al., *Nucleic Acids Res*. 18:5433, 1990; and Wincott et al., *Nucleic Acids Res*. 23:2677-2684, 1995; Wincott et al., *Methods Mol. Bio*. 74:59, 1997.

In certain embodiments, the nucleic acid molecules of the present disclosure can be synthesized separately and joined together post-synthetically, for example, by ligation (Moore et al., *Science* 256:9923, 1992; Draper et al., PCT Publication No. WO 93/23569; Shabarova et al., *Nucleic Acids Res*. 19:4247, 1991; Bellon et al., *Nucleosides & Nucleotides* 16:951, 1997; Bellon et al., *Bioconjugate Chem*. 8:204, 1997), or by hybridization following synthesis or deprotection.

A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res*. 18:6353, 1990, and *Nucleic Acids Res*. 15:3113, 1987; Cload and Schepartz, *J. Am. Chem. Soc*. 113:6324, 1991; Richardson and Schepartz, *J. Am. Chem. Soc*. 113:5109, 1991; Ma et al., *Nucleic Acids Res*. 21:2585, 1993, and *Biochemistry* 32:1751, 1993; Durand et al., *Nucleic Acids Res*. 18:6353, 1990; McCurdy et al., *Nucleosides & Nucleotides* 10:287, 1991; Jaschke et al., *Tetrahedron Lett*. 34:301, 1993; Ono et al., *Biochemistry* 30:9914, 1991; Arnold et al., PCT Publication No. WO 89/02439; Usman et al., PCT Publication No. WO 95/06731; Dudycz et al., PCT Publication No. WO 95/11910 and Ferentz and Verdine, *J. Am. Chem. Soc*. 113:4000, 1991.

In some embodiments, the synthesis of a dsRNA molecule of this disclosure, which can be further modified, comprises: (a) synthesis of a first (antisense) strand and synthesis of a second (sense) strand and a third (sense) strand that are each complementary to non-overlapping regions of the first strand; and (b) annealing the first, second and third strands together under conditions suitable to obtain a dsRNA molecule. In another embodiment, synthesis of the first, second and third strands of a dsRNA molecule is by solid phase oligonucleotide synthesis. In yet another embodiment, synthesis of the first, second, and third strands of a dsRNA molecule is by solid phase tandem oligonucleotide synthesis.

A nucleic acid molecule may contain substitutions or modifications of the base, sugar, phosphate, or any combination thereof. Some examples of substitutions and chemical modifications to the base, phosphate, or sugar moieties of nucleic acid molecules are given in the following: See, e.g., Eckstein et al., PCT Publication No. WO 92/07065; Perrault et al., *Nature* 344:565, 1990; Pieken et al., *Science* 253:314, 1991; Usman and Cedergren, *Trends in Biochem. Sci*. 17:334, 1992; Usman et al., *Nucleic Acids Symp. Ser*. 31:163, 1994; Beigelman et al., *J. Biol. Chem*. 270:25702, 1995; Burgin et al., *Biochemistry* 35:14090, 1996; Burlina et al., *Bioorg. Med. Chem*. 5:1999, 1997; Thompson et al., Karpeisky et al., *Tetrahedron Lett*. 39:1131, 1998; Earnshaw and Gait, *Biopolymers (Nucleic Acid Sciences)* 48:39-55, 1998; Verma and Eckstein, *Annu. Rev. Biochem*. 67:99-134, 1998; Herdewijn, *Antisense Nucleic Acid Drug Dev*. 10:297, 2000; Kurreck, *Eur. J. Biochem*. 270:1628, 2003; Dorsett and Tuschl, *Nature Rev. Drug Discov*. 3:318, 2004; PCT Publication Nos. WO 91/03162; WO 93/15187; WO 97/26270; WO 98/13526; U.S. Pat. Nos. 5,334,711; 5,627,053; 5,716,824; 5,767,264; 6,300,074.

Modifications may include internucleoside linkages, such as phosphorothioate, or 5-methyluridine in place of uridine.

In one embodiment, this disclosure features substituted or modified dsRNA molecules, such as phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, or alkylsilyl substitutions.

Some oligonucleotide backbone modifications are given in Hunziker and Leumann, *Nucleic Acid Analogues: Synthesis and Properties, in Modern Synthetic Methods, VCH*, 331-417, 1995; and Mesmaeker et al., *ACS*, 24-39, 1994.

Therapeutics

In another aspect, this disclosure provides a method for reducing the expression of a gene or reducing the function an endogenous nucleic acid based regulatory system of a cell, comprising administering a nucleic acid compound as described herein to a cell, wherein the nucleic acid compound reduces the expression of the gene in the cell.

In another aspect, this disclosure provides a method for reducing the function of an endogenous nucleic acid based regulatory system of a cell, comprising administering a nucleic acid compound described herein to a cell, wherein the nucleic acid compound reduces the function of the endogenous nucleic acid based regulatory system in the cell.

In another aspect, this disclosure provides a method for treating or managing a disease or condition in a subject associated, linked, and/or resulting from aberrant nucleic acid expression, comprising administering to the subject in need of treatment or management a nucleic acid compound as disclosed herein, wherein the nucleic acid compound reduces the expression or function of the nucleic acid thereby treating or managing the disease or condition.

Definitions

As used herein, the term "linked" encompasses a covalent linkage either directly between two chemical entities (e.g., RNA and a hydroxymethyl substituted nucleomonomer), or indirectly between two chemical entities, for example via a linker.

As used herein, the term "nucleobase analog" refers to a substituted or unsubstituted nitrogen-containing parent heteroaromatic ring that is capable of forming Watson-Crick hydrogen bonds with a complementary nucleobase or nucleobase analog. Exemplary nucleobase analogs include, but are not limited to, 7-deazaadenine, inosine, nebularine, nitropyrrole, nitroindole, 2-aminopurine, 2,6-diaminopurine, hypoxanthine, pseudouridine, 5-propynylcytidine, isocytidine, isoguanine, 7-deazaguanine, 2-thiopyrimidine, 6-thioguanine, 4-thiothymine, 4-thiouracil, $O^6$-methyl guanine, $N^6$-methyl adenine, $O^4$-methyl thymine, 5,6-dihydrothymine, 5,6-dihydrouracil, 4-methylindole, ethenoadenine. Additional exemplary nucleobase analogs can be found in Fasman, 1989, Practical Handbook of Biochemistry and Molecular Biology, pp. 385-394, CRC Press, Boca Raton, Fla., and the references cited therein, incorporated herein by reference.

As used herein, the term "nucleomonomer" means a moiety comprising (1) a base covalently linked to (2) a second moiety. Nucleomonomers can be linked to form oligomers that bind to target or complementary base sequences in nucleic acids in a sequence specific manner. Nucleomonomers may be nucleosides, nucleotides, non-nucleotides or non-nucleosides (e.g. hydroxymethyl substituted nucleomonomer).

As used herein, the terms "conformationally restricted nucleomonomer", "conformationally restricted nucleotide" may be used interchangeably and refer to a nucleomonomer that has a bicyclic sugar moiety (e.g. bicyclic ribose) wherein the C2' and C4' of the sugar moiety are bridged (e.g., Monomer R) or the C3' and C5' are bridged (e.g., Monomer Q).

As used herein, the terms "hydroxymethyl substituted nucleomonomer", "hydroxymethyl nucleomonomer", "hydroxymethyl monomer", "acyclic nucleomonomer", "acyclic monomer", "acyclic hydroxymethyl substituted nucleomonomer" may be used interchangeably throughout.

As used herein, the terms "RISC length" or "RISC length RNA complex" means a nucleic acid molecule having less than 25 base pairs.

As used herein, the term "overhang" (e.g., 3'-end overhang or 3' overhang) means an unpaired region of a nucleic acid compound which may contain all nucleotides, non-nucleotides (e.g., hydroxymethyl substituted nucleomonomers), or a combination of nucleotides and non-nucleotides.

As used herein the terms "Dicer length" or "Dicer length RNA complex" means a nucleic acid molecule have 25 or more base pairs, generally, from 25 to 40 base pairs.

As used herein the term "bifunctional nucleic acid compound" or "bifunctional RNA complex" or "bifunctional dsRNA" means a nucleic acid compound having a sense strand and antisense strand, wherein the sense strand and the antisense strand are each complementary to different regions of the same target RNA (i.e., a first region and a second region), or are each complementary to a region of at least two different target RNAs.

As used herein, the terms "seed region" or "seed sequence" refer to the region of a microRNA that is implicated in gene regulation by inhibition of translation and/or mRNA degradation, or the portion of the guide strand in a siRNA that is analogous to the seed region of a microRNA By "ribonucleic acid" or "RNA" is meant a nucleic acid molecule comprising at least one ribonucleotide molecule. As used herein, "ribonucleotide" refers to a nucleotide with a hydroxyl group at the 2'-position of a β-D-ribofuranose moiety. The term RNA includes double stranded (ds) RNA, single-stranded (ss) RNA, isolated RNA (such as partially purified RNA, essentially pure RNA, synthetic RNA, recombinantly produced RNA), altered RNA (which differs from naturally occurring RNA by the addition, deletion, substitution or alteration of one or more nucleotides), or any combination thereof. For example, such altered RNA can include addition of non-nucleotide material, such as at one or both ends of an RNA molecule, internally at one or more nucleotides of the RNA, or any combination thereof. Nucleotides in RNA molecules of the instant disclosure can also comprise non-standard nucleotides, such as naturally occurring nucleotides, non-naturally occurring nucleotides, chemically-modified nucleotides, deoxynucleotides, or any combination thereof. These altered RNAs may be referred to as analogs or analogs of RNA containing standard nucleotides (i.e., standard nucleotides, as used herein, are considered to be adenine, cytidine, guanidine, thymidine, and uridine).

The term "dsRNA" and "RNA complex" as used herein, refers to any nucleic acid molecule comprising at least one ribonucleotide molecule and capable of inhibiting or down regulating gene expression, for example, by promoting RNA interference ("RNAi") or gene silencing in a sequence-specific manner. The dsRNAs (mdRNAs) of the instant disclosure may be suitable substrates for Dicer or for association with RISC to mediate gene silencing by RNAi. Examples of dsRNA molecules of this disclosure are provided in the Sequence Listing identified herein. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, and non-nucleotides. In certain embodiments, dsRNA molecules comprise ribonucleotides up to about 100% of the nucleotide positions.

In addition, as used herein, the term "RNAi" is meant to be equivalent to other terms used to describe sequence specific RNA interference, such as post transcriptional gene silencing, translational inhibition, or epigenetics. For example, dsRNA molecules of this disclosure can be used to epigenetically silence genes at the post-transcriptional level or the pre-transcriptional level or any combination thereof.

The term "gene" as used herein, especially in the context of "target gene" or "gene target" for RNAi, means a nucleic acid molecule that encodes an RNA or a transcription product of such gene, including a messenger RNA (mRNA, also referred to as structural genes that encode for a polypeptide), an mRNA splice variant of such gene, a functional RNA (fRNA), or non-coding RNA (ncRNA), such as small temporal RNA (stRNA), microRNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for dsRNA mediated RNAi to alter the activity of the target RNA involved in functional or regulatory cellular processes.

As used herein, "gene silencing" refers to a partial or complete loss-of-function through targeted inhibition of gene expression in a cell, which may also be referred to as RNAi "knockdown," "inhibition," "down-regulation," or "reduction" of expression of a target gene. Depending on the circumstances and the biological problem to be addressed, it may be preferable to partially reduce gene expression. Alternatively, it might be desirable to reduce gene expression as much as possible. The extent of silencing may be determined by methods described herein and known in the art (see, e.g., PCT Publication No. WO 99/32619; Elbashir et al., *EMBO J.* 20:6877, 2001). Depending on the assay, quantification of gene expression permits detection of various amounts of inhibition that may be desired in certain embodiments of this disclosure, including prophylactic and therapeutic methods, which will be capable of knocking down target gene expression, in terms of mRNA level or protein level or activity, for example, by equal to or greater than 10%, 30%, 50%, 75% 90%, 95% or 99% of baseline (i.e., normal) or other control levels, including elevated expression levels as may be associated with particular disease states or other conditions targeted for therapy.

Chemical Definitions

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure. As described herein, all value ranges are inclusive over the indicated range. Thus, a range of $C_1$-$C_4$ will be understood to include the values of 1, 2, 3, and 4, such that $C_1$, $C_2$, $C_3$ and $C_4$ are included.

The term "alkyl" as used herein refers to a saturated, branched or unbranched, substituted or unsubstituted aliphatic group containing from 1-22 carbon atoms (1, 2, 3, 4, 5, 6, 7, 8, 9, 10, 11, 12, 13, 14, 15, 16, 17, 18, 19, 20, 21, or 22 carbon atoms). This definition applies to the alkyl portion of other groups such as, for example, alkoxy, alkanoyl, aralkyl, and other groups defined below. The term "cycloalkyl" as used herein refers to a saturated, substituted or unsubstituted cyclic alkyl ring containing from 3 to 12 carbon atoms.

The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrathydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula —C(=O)OH or —C(=O)O⁻. The terms "carbonyl" and "acyl" as used herein refer to a group in which an oxygen atom is double bonded to a carbon atom >C=O. The term "hydroxyl" as used herein refers to —OH or —O⁻. The term "nitrile" or "cyano" as used herein refers to —CN. The term "halogen" or "halo" refers to fluoro (—F), chloro (—Cl), bromo (—Br), and iodo (—I).

The term "cycloalkyl" as used herein refers to a saturated cyclic hydrocarbon ring system containing from 3 to 12 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl. In another embodiment, the (cycloalkyl)alkyl groups contain from 3 to 12 carbon atoms in the cyclic portion and 1 to 6 carbon atoms in the alkyl portion. In certain embodiments, the (cycloalkyl)alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(=O)— alkyl groups, each optionally containing 2 to 10 carbon atoms. Specific embodiments of alkanoyl and alkanoyloxy groups are acetyl and acetoxy, respectively.

The term "alkynyl" as used herein refers to an unsaturated branched, straight chain, or cyclic alkyl group having 2 to 10 carbon atoms and having at least one carbon-carbon triple bond derived by the removal of one hydrogen atom from a single carbon atom of a parent alkyne. Exemplary alkynyls include ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, 2-decynyl, or the like. The alkynyl group may be substituted or unsubstituted.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" as used herein refers to the group —NRR', where R and R' may independently be hydrogen or ($C_1$-$C_4$) alkyl.

The term "alkylaminoalkyl" refers to an alkylamino group linked via an alkyl group (i.e., a group having the general structure -alkyl-NH-alkyl or -alkyl-N(alkyl)(alkyl)). Such groups include, but are not limited to, mono- and di-($C_1$-$C_8$ alkyl)amino$C_1$-$C_8$ alkyl, in which each alkyl may be the same or different.

The term "dialkylaminoalkyl" refers to alkylamino groups attached to an alkyl group. Examples include, but are not limited to, N,N-dimethylaminomethyl, N,N-dimethylaminoethyl N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, or the like.

The term "carboxyalkyl" as used herein refers to the substituent —$R^{10}$—COOH, wherein $R^{10}$ is alkylene; and "carbalkoxyalkyl" refers to —$R^{10}$—C(=O)O$R^{11}$, wherein $R^{10}$ and $R^{11}$ are alkylene and alkyl respectively. In certain embodiments, alkyl refers to a saturated straight- or branched-chain hydrocarbyl radical of 1 to 6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxy" includes substituted and unsubstituted alkyl, alkenyl, and alkynyl groups covalently linked to an oxygen atom. In one embodiment, the alkoxy group contains 1 to about 10 carbon atoms. Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "alkoxyalkyl" refers to an alkylene group substituted with an alkoxy group. For example, methoxyethyl ($CH_3OCH_2CH_2$—) and ethoxymethyl ($CH_3CH_2OCH_2$—) are both $C_3$ alkoxyalkyl groups.

The term "aroyl," as used alone or in combination herein, refers to an aryl radical derived from an aromatic carboxylic acid, such as optionally substituted benzoic or naphthoic acids.

The term "aralkyl" as used herein refers to an aryl group bonded to the 2-pyridinyl ring or the 4-pyridinyl ring through an alkyl group, preferably one containing 1 to 10 carbon atoms. A preferred aralkyl group is benzyl.

The term "carboxy," as used herein, represents a group of the formula —C(=O)OH or —C(=O)O$^-$.

The term "carbonyl" as used herein refers to a group in which an oxygen atom is double bonded to a carbon atom —C=O.

The term "trifluoromethyl" as used herein refers to —$CF_3$.

The term "trifluoromethoxy" as used herein refers to —$OCF_3$.

The term "hydroxyl" as used herein refers to —OH or —O$^-$.

The term "nitrile" or "cyano" as used herein refers to the group —CN.

The term "nitro," as used herein alone or in combination refers to a —$NO_2$ group.

The term "amino" as used herein refers to the group —$NR^9R^9$, wherein $R^9$ may independently be hydrogen, alkyl, aryl, alkoxy, or heteroaryl. The term "aminoalkyl" as used herein represents a more detailed selection as compared to "amino" and refers to the group —NR'R', wherein R' may independently be hydrogen or ($C_1$-$C_4$) alkyl. The term "dialkylamino" refers to an amino group having two attached alkyl groups that can be the same or different.

The term "alkanoylamino" refers to alkyl, alkenyl or alkynyl groups containing the group —C(=O)— followed by —N(H)—, for example acetylamino, propanoylamino and butanoylamino and the like.

The term "carbonylamino" refers to the group —NR'—CO—$CH_2$—R', wherein R' may be independently selected from hydrogen or ($C_1$-$C_4$) alkyl.

The term "carbamoyl" as used herein refers to —O—C(O)$NH_2$.

The term "carbamyl" as used herein refers to a functional group in which a nitrogen atom is directly bonded to a carbonyl, i.e., as in —NR"C(=O)R" or —C(=O)NR"R", wherein R" can be independently hydrogen, alkyl, substituted alkyl, alkenyl, substituted alkenyl, alkoxy, cycloalkyl, aryl, heterocyclo, or heteroaryl.

The term "alkylsulfonylamino" refers to the group —NHS(O)$_2$$R^{12}$, wherein $R^{12}$ is alkyl.

The term "halogen" as used herein refers to bromine, chlorine, fluorine or iodine. In one embodiment, the halogen is fluorine. In another embodiment, the halogen is chlorine.

The term "heterocyclo" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2, or 3 heteroatoms selected from nitrogen, oxygen or sulfur. Plural heteroatoms in a given heterocyclo ring may be the same or different.

Exemplary monocyclic heterocyclo groups include pyrrolidinyl, pyrrolyl, indolyl, pyrazolyl, imidazolyl, oxazolyl, isoxazolyl, thiazolyl, furyl, tetrahydrofuryl, thienyl, piperidinyl, piperazinyl, azepinyl, pyrimidinyl, pyridazinyl, tetrahydropyranyl, morpholinyl, dioxanyl, triazinyl and triazolyl. Preferred bicyclic heterocyclo groups include benzothiazolyl, benzoxazolyl, benzothienyl, quinolinyl, tetrahydroisoquinolinyl, benzimidazolyl, benzofuryl, indazolyl, benzisothiazolyl, isoindolinyl and tetrahydroquinolinyl. In more detailed embodiments heterocyclo groups may include indolyl, imidazolyl, furyl, thienyl, thiazolyl, pyrrolidyl, pyridyl and pyrimidyl.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., BLASTN, see Altschul et al., *J. Mol. Biol.* 215:403-410, 1990).

"Aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chem.* 45:1628, 1999).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation —$CH_2CH_3$, —$CHFCH_3$, —$CF_2CH_3$, —$CHFCH_2F$, —$CHFCHF_2$, —$CHFCF_3$, —$CF_2CH_2F$, —$CF_2CHF_2$, —$CF_2CF_3$, and other variations as described above. Representative substituents include —X, —$R^6$, —O—, =O, —OR, —$SR^6$, —S—, =S, —$NR^6R^6$, =$NR^6$, —$CX_3$, —$CF_3$, —CN, —OCN, —SCN, —NO, —$NO_2$, =$N_2$, —$N_3$, —S(=O)$_2$O—, —S(=O)$_2$OH, —S(=O)$_2R^6$, —OS(=O)$_2$O—, —OS(=O)$_2$OH, —OS(=O)$_2R^6$, —P(=O)(O$^-$)$_2$, —P(=O)(OH)(O$^-$), —OP(=O)$_2$(O$^-$), —C(=O)$R^6$, —C(=S)$R^6$, —C(=O)O$R^6$, —C(=O)O$^-$, —C(=S)O$R^6$, —$NR^6$—C(=O)—N($R^6$)$_2$, —$NR^6$—C(=S)—N($R^6$)$_2$, and —C(=N$R^6$)N$R^6R^6$, wherein each X is independently a halogen; and each $R^6$ is independently hydrogen, halogen, alkyl, aryl, arylalkyl, arylaryl, arylheteroalkyl, heteroaryl, heteroarylalkyl, N$R^7R^7$, —C(=O)$R^7$, and —S(=O)$_2R^7$; and each $R^7$ is independently hydrogen, alkyl, alkanyl, alkynyl, aryl, arylalkyl, arylheteralkyl, arylaryl, heteroaryl or heteroarylalkyl. Aryl containing substituents, whether or not having one or more substitutions, may be attached in a para (p-), meta (m-) or ortho (o-) conformation, or any combination thereof. In general, substituents may be further substituted with any atom or group of atoms.

For example purposes only, the position of a nucleomonomer in a strand may be described as follows where X represents any type of nucleomonomer (e.g., nucleoside, modified nucleotide, RNA, DNA, hydroxymethyl substituted nucleomonomer or conformationally restricted nucleomonomer) and the number represents the position of that nucleomonomer in the strand. For example, X1 represents position one of the strand below counting from the 5'-end of the strand; X7 represents position seven of the strand below counting from the 5'-end of the strand. Alternatively, X1, X2, and X3 represent the last three positions at the 5'-end of the strand below, and X1 to X10 represent the last ten positions at the 5'-end of the strand. The $X_n$ may represent positions 11 to 60 (or n=1 to 60), thus when n is 20 (or X20), this indicates position 20 of the strand counting from the 5'-end of the strand.

```
5' X1-X2-X3-X4-X5-X6-X7-X8-X9-X10-X_n 3'
```

The same approach may be taken by counting from the 3'-end of a strand in order to identify the position of a nucleomonomer in the strand (example strand shown below). For the strand below, the position of a nucleomonomer in the strand may be described as follows where X represents any type of nucleomonomer (e.g., nucleoside, modified nucleotide, RNA, DNA, hydroxymethyl substituted nucleomonomer or conformationally restricted nucleomonomer) and the number represents the position of that nucleomonomer in the strand. For example, X1 represents position one of the strand below counting from the 3'-end of the strand; X7 represents position seven of the strand below counting from the 3'-end of the strand. Alternatively, X1, X2, and X3 represent the last three positions at the 3'-end of the strand below, and X1 to X10 represent the last ten positions at the 3'-end of the strand. The $X_n$ may represent positions 11 to 60 (or n=1 to 60), thus when n is 20 (or X20), this indicates position 20 of the strand counting from the 3'-end of the strand.

```
5' X_n-X10-X9-X8-X7-X6-X5-X4-X3-X2-X1 3'
```

Alternative Embodiments

All publications, non-patent publications, references, patents, patent publications, patent applications and other literature cited herein are each hereby specifically incorporated by reference in its entirety.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

The use of the alternative, for example "or," should be understood to mean either one, both, or any combination thereof of the alternatives.

It should be understood that the terms "a" and "an" as used herein refer to "one or more" of the enumerated components. The use herein of the terms "a," "an," "the" and similar terms in describing the disclosure, and in the claims, are to be construed to include both the singular and the plural.

The terms "comprising," "having," "including" and "containing" are to be construed as open-ended terms which mean, for example, "including, but not limited to." Thus, terms such as "comprising," "having," "including" and "containing" are to be construed as being inclusive, not exclusive. As used herein, the terms "include" and "comprise" are open ended and are used synonymously.

Recitation of a range of values herein refers individually to each and any separate value falling within the range as if it were individually recited herein, whether or not some of the values within the range are expressly recited. For example, the range "4 to 12" includes without limitation the values 5, 5.1, 5.35 and any other whole, integer, fractional, or rational value greater than or equal to 4 and less than or equal to 12. Specific values employed herein will be understood as exemplary and not to limit the scope of the disclosure.

Recitation of a range of number of carbon atoms herein refers individually to each and any separate value falling within the range as if it were individually recited herein, whether or not some of the values within the range are expressly recited. For example, the term "C1-24" includes without limitation the species C1, C2, C3, C4, C5, C6, C7, C8, C9, C10, C11, C12, C13, C14, C15, C16, C17, C18, C19, C20, C21, C22, C23, and C24.

Definitions of technical terms provided herein should be construed to include without recitation those meanings associated with these terms known to those skilled in the art, and are not intended to limit the scope of the disclosure. Definitions of technical terms provided herein shall be construed to dominate over alternative definitions in the art or definitions which become incorporated herein by reference to the extent that the alternative definitions conflict with the definition provided herein.

The examples given herein, and the exemplary language used herein are solely for the purpose of illustration, and are not intended to limit the scope of the disclosure.

When a list of examples is given, such as a list of compounds or molecules suitable for this disclosure, it will be apparent to those skilled in the art that mixtures of the listed compounds or molecules are also suitable.

EXAMPLES

Example 1

Synthesis of 2,2'-Anhydro-5-methyluracil

5-Methyl uridine (56.0 g, 217 mmol) and diphenyl carbonate (69.7 g, 325 mmol) were dissolved in DMF (250 mL) after which sodium bicarbonate (1.82 g, 22 mmol) was added to the solution. The resulting suspension was immersed in an oil bath and heated with stirring for 2.5-3 hrs at 110° C. until cessation of $CO_2$ evolution was observed. After cooling to room temperature the reaction mixture was concentrated to half volume and then slowly poured into rapidly stirring diethyl ether (800 mL) generating a white solid. After decanting the ether the white solid was washed with additional fresh ether (3×500 mL). The resulting solid was filtered, and washed with ether. A final precipitation was done by dissolving the isolated white solid in hot methanol (250 mL) and allowing the solution to cool to room temperature. Product was precipitated by addition of ether (250 mL), and then cooled at 0° C. overnight. The white solid was isolated by filtration and dried on high vacuum to generate 2,2'-Anhydro-5-methyluracil (39.2 g, 75%) as a white powder.

Example 2

Synthesis of 1-[5-O-(4-methoxytrityl)-2-deoxy-2-vinyl-β-D-ribo-pentofuranosyl]-thymine A suspension of 2,2'-anhydro-5-methyluracil (41.0 g, 171 mmol), p-tosic acid mono hydrate (32.5 g, 171 mmol), and NaI (25.6 g, 171 mmol) in acetone (700 mL) was stirred at 55° C. for 4 h. After cooling to room temperature the resulting precipitates were filtered and washed with acetone. The collected filtrate was concentrated to approximately 20% volume. Saturated $Na_2S_2O_3$ (50 mL) was then added in approximately 5 mL portions and the mixture was shaken and sonicated until the brownish solution faded to a pale yellow solution. The resulting precipitate was filtered and the isolated filtrate concentrated in vacuo to give a yellow gummy foam. The residue was then dissolved in acetonitrile (350 mL), after which additional white precipitate was removed by filtration. The isolated filtrate was concentrated in vacuo to give crude 1-(2-deoxy-2-iodo-β-D-ribofuranosyl)-5-methyluracil as a yellow foam (62.2 g crude). Crude 1-(2-deoxy-2-iodo-β-D-ribofuranosyl)-5-methyluracil (62.2 g, 169 mmol) was dissolved in anhydrous pyridine (800 mL) and 4-methoxytritylchloride (57.4 g, 186 mmol) was added. The reaction mixture was allowed to stir overnight at room temperature under nitrogen. The solution was concentrated in vacuo and then partitioned between EtOAc (400 mL) and water (400 mL). After separation, the aqueous layer was washed with additional EtOAc (400 mL). The combined organic phases were washed with brine (400 mL), dried over Na2SO4, filtered and evaporated to dryness under reduced pressure. The resulting foamy brown residue was dried under high vacuum overnight providing 115.9 g of crude intermediate 1-[5-O-(4-methoxytrityl)-2-deoxy-2-iodo-β-D-ribofuranosyl] 5-methyluracil. This crude material (115.9 g, 181 mmol) was dissolved in toluene (1.5 L) after which DMAP (6.63 g, 54 mmol) and TEA (75 mL, 543 mmol) were added. The resulting reaction mixture was allowed to stir under nitrogen for 10 minutes, after which chlorodimethylvinylsilane (75 mL, 543 mmol) was added dropwise via addition funnel.

The reaction was stirred under nitrogen at room temp for 1 h, and then quenched by addition of MeOH (20 mL). After allowing the solution to stir for an additional 10 minutes, the mixture was evaporated to a semi-solid residue which was then partitioned between EtOAc (1600 mL) and cold brine (1800 mL). After separation the organic layer was washed with additional cold brine (1800 mL). The combined aqueous layers were then back extracted with EtOAc (500 mL). The combined organic phases were washed with cold brine (1 L), dried over $Na_2SO_4$, filtered, and evaporated to dryness to give crude intermediate 1-[5-O-(4-methoxytrityl)-2-deoxy-2-iodo-3-(dimethyl)vinylsilyl-β-D-ribo-pentofuranosyl]-thymine 3 (112 g) as a brown foam. This material was used as is for the vinyl transfer reaction to generate 1-[5-O-(4-methoxytrityl)-2-deoxy-2-vinyl-β-D-ribo-pentofuranosyl]-thymine 4.

To a solution of crude 3 (125.7 g, 173.4 mmol) in benzene (1.7 L) was added 2,2'-azobis(2-methylproprionitrile) (17.09 g, 104 mmol) and hexamethylditin (25.18 mL, 121.42 mmol). The resulting solution was immersed in an oil bath and heated with stirring for 2.5 h at reflux, after which the mixture was removed from heat and allowed to cool to room temperature. Additional 2,2'-azobis(2-methylproprionitrile) (8.55 g, 52.04 mmol) and hexamethylditin (12.59 mL, 60.71 mmol) was then added and the reaction heated back to reflux. After stirring for an additional 2.5 h, the mixture was removed from heat and allowed to stir at room temperature overnight. The reaction was then concentrated in vacuo and dissolved in THF (1.7 L). Tetrabutylammoniumflouride in THF (1 M, 260.19 mL, 260.19 mmol) was added to the reaction mixture. After allowing the mixture to stir at room temperature for 1 h, the THF was evaporated to produce 260.31 g of crude reaction mixture. The crude material was purified by $SiO_2$ chromatography (50/50 EtOAc/Et2O) to yield 4 (23.4 g, 25%). ES/MS (M-H) m/z: 539.

Example 3

Synthesis of 1-[3-O-Benzyl-2-deoxy-2-vinyl-β-D-ribo-pentofuranosyl]thymine

Compound 4 (22.5 g, 42 mmol) was dissolved in THF (140 mL) under nitrogen, cooled in ice bath to −10° C., after which sodium hydride (60% dispersion in mineral oil) (5.0 g, 125 mmol) was added portionwise. The reaction mixture was stirred for 30 minutes before slow dropwise addition of benzyl bromide (4.95 mL, 42 mmol). Stirring was continued at −10° C. for 1 h, after which the reaction vessel was kept with stirring for 18 h at 4° C. Progress of the reaction was monitored with LCMS (see spectra below). The reaction mixture was then quenched with water (5 mL added dropwise) while still cold after which EtOAc (150 mL) and water (150 mL) were added. Upon phase separation the aqueous layer was back extracted with EtOAc (100 mL). The combined organic phases were washed with sat. $NaHCO_3$ (200 mL), water (200 mL), brine (200 mL), dried over $Na_2SO_4$, filtered and concentrated to provide 27.6 g of crude product 1-[5-O-(4-methoxytrityl)-3-O-Benzyl-2-deoxy-2-vinyl-β-D-ribo-pentofuranosyl]thymine. This material was directly dissolved in EtOAc (70 mL), cooled in ice bath to 0° C., after which 1M HCl in EtOAc (200 mL) was added. After 2 h the reaction mixture was slowly neutralized with 210 mL of 2M NaOH, and after phase separation the organic layer was washed with brine (200 mL), dried and concentrated. Crude product was purified by $SiO_2$ chromatography (10%-60% ACN/DCM v/v) to give 1-[3-O-Benzyl-2-deoxy-2-vinyl-β-D-ribo-pentofuranosyl]thymine 5 as a white foam (7.75 g, 53%). ES/MS (M-H) m/z: 357.

Example 4

Synthesis of 1-[3-O-Benzyl-4-C-hydroxymethyl-2-deoxy-2-vinyl-β-D-ribo-pentofuranosyl]thymine A solution of Dess-Martin Periodinane (11.0 g, 26 mmol) in DCM (145 mL) was added to a solution of alcohol 5 in DCM (145 mL) at 0° C., and the mixture was stirred vigorously for 2.5 h. The reaction mixture was then diluted with DCM (100 mL) and 4% aq. $Na_2S_2O_3$ (400 mL) and then stirred for 15 min. After separation, the aqueous layer was back extracted with DCM (200 mL), and the combined organic phases were washed with sat. $NaHCO_3$ (400 mL), brine (400 mL), dried over $Na_2SO_4$, filtered and evaporated to dryness. The resulting white foam was dissolved in 1,4-dioxane (145 mL). Formaldehyde (37% aq. solution) (25 mL, 325 mmol) and sodium hydroxide solution (65 mL, 2M) were added, and the mixture was vigorously stirred for 15 h. Saturated $NaHCO_3$ (20 mL/1.5 g of alcohol 5) was added, and after stirring for 5 min the suspension was evaporated to dryness, suspended (with sonication) and co-evaporated with acetonitrile (150 mL), suspended in methanol (100 mL) and evaporated on silica gel. The residue was loaded on thin pad of Celite and product was pre-purified by filtration with 1 L of DCM:MeOH=7:3. Product was purified by $SiO_2$ gel chromatography (0-15% MeOH/DCM) to yield 1-[3-O-Benzyl-4-C-hydroxymethyl-2-deoxy-2-vinyl-β-D-ribo-pentofuranosyl]thymine 6 as a white foam (5.5 g, 67%). ES/MS (M-H) m/z: 387.

Example 5

Synthesis of 1-[4',5'-(1,1,3,3-Tetraisopropyldisiloxane-1,3-diyl)-3-O-Benzyl-2-deoxy-2-vinyl-β-D-ribo-pentofuranosyl]thymine Diol 6 (5.5 g, 14 mmol) was dissolved in anhydrous pyridine (50 mL) and 1,3-dichloro-1,1,3,3-tetraisopropyldisiloxane (6.33 mL, 20 0 mmol) was added dropwise at room temperature under $N_2$ atmosphere. Stirring was continued for 3 h, after which solvent was removed under reduced pressure and the residue partitioned between EtOAc and sat. $NaHCO_3$. The aqueous layer was back extracted with EtOAc, and the combined organic layers were washed with water, brine, dried and evaporated to dryness. Crude product was purified by $SiO_2$ gel chromatography (0-60% EtOAc/Hexanes v/v) to generate 1-[4',5'-(1,1,3,3-Tetraisopropyldisiloxane-1,3-diyl)-3-O-Benzyl-2-deoxy-2-vinyl-β-D-ribo-pentofuranosyl]thymine 7 as a white foam (7.7 g, 86%) ES/MS (M-H) m/z: 630.

Example 6

Synthesis of 1-[4',5'-(1,1,3,3-Tetraisopropyldisiloxane-1,3-diyl)-3-O-Benzyl-2-deoxy-2-hydroxymethyl-β-D-ribo-pentofuranosyl]thymine A solution of compound 7 (2 g, 3.17 mmole) in dry $CH_2Cl_2$ (63 mL) was cooled to −78° C. in dry ice/acetone bath. Ozone containing air was bubbled through the cooled solution for 60 minutes (compressed air flow rate of 5 SCFH and $O_3$ production rate of 12.5 mmole/h or 0.6 g/h). The solution was then added to a cooled mixture (0° C.) of sodium borohydride (0.959 g, 25.4 mmole) in MeOH (63 mL), and allow to react for 20 min at room temperature. The reaction was quenched with citric acid (2.4 g, 12.7 mmole) and evaporated to dryness in vacuo. The crude residue was dissolved in EtOAc (60 mL) and washed with water (2×60 mL). The combined aqueous phases were back extracted with EtOAc (40 mL), after which the combined organic layers were washed with brine (60 mL), and subsequently dried over $Na_2SO_4$, filtered, and evaporated to a white film. The crude material was purified by silica gel chromatography (20%-80% EtOAc/Hexane v/v), yielding compound 1-[4',5'-(1,1,3,3-Tetraisopropyldisiloxane-1,3-diyl)-3-O-Benzyl-2-deoxy-2-hydroxymethyl-β-D-ribo-pentofuranosyl]thymine 8 (1.01 g, 50%). ES/MS (M-H) m/z: 633. A yield of 60% has also been obtained for synthesis of 8.

Example 7

Synthesis of 1-[3-O-Benzyl-4-C-hydroxymethyl-2-deoxy-2-acetoxymethyl-β-D-ribo-pentofuranosyl]thymine To a solution of 8 (1.72 g, 2.72 mmol) in dry pyridine (30 mL) was added dropwise acetic anhydride (0.31 mL, 3.26 mmol), under a nitrogen atmosphere. Stirring was continued overnight, at room temperature. Solvent was removed in vacuo and the residue partitioned between EtOAc (150 mL) and sat. $NaHCO_3$ (150 mL). The aqueous layer was back extracted with additional EtOAc (100 mL), and the combined organic layers were washed with water (100 mL), brine (100 mL), dried ($Na_2SO_4$) and evaporated to dryness. Crude product was purified by $SiO_2$ column chromatography (10%-60% EtOAc/Hexanes v/v) to give the intermediate acetate (1.28 g, 70%) as a white foam. The purified acetylated 8 (1.28 g, 1.9 mmol) was dissolved in buffered TBAF (prepared by addition of 1M AcOH (50 mL) in THF to 1M TBAF (50 mL) in THF) at room temperature. After 1 h stirring solvent was removed under reduced pressure and the residue purified on $SiO_2$ column chromatography (0-5% MeOH/DCM) to yield 1-[3-O-Benzyl-4-C-hydroxymethyl-2-deoxy-2-acetoxymethyl-β-D-ribo-pentofuranosyl]thymine 9 (0.63 g, 77%) as an off white foam. ES/MS (M-H) m/z: 433.

Example 8

Synthesis of (1R,3R,4R,8S)-1-benzoyloxymethyl-8-benzyloxy-3-(thymin-1-yl)-2,6-dioxabicyclo[3,2,1]octane To a solution of compound 9 (0.64 g, 1.46 mmol) in anhydrous pyridine (15 mL) was added methanesulfonyl chloride (0.25 mL, 3.22 mmol) dropwise at room temperature under nitrogen atmosphere. The mixture was stirred overnight at ambient temperature. Solvent was removed under reduced pressure and the residue taken partitioned between EtOAc (100 mL) and sat. $NaHCO_3$ (80 mL). The aqueous layer was back extracted with EtOAc (60 mL), and the combined organic phases were washed with water (100 mL) and brine (100 mL), dried ($Na_2SO_4$) and concentrated to a gum. Crude product was co-evaporated from acetonitrile (2×50 mL) and used without further purification for the next step. The crude bismesylate was dissolved in a dioxane/water mixture (15 mL) and 2 M sodium hydroxide (15 mL) was added. After 20 min stirring at room temperature the reaction vessel was transferred to an oil bath and heated at 60° C. for 1 h. Solvent was removed under reduced pressure and the residue taken between EtOAc (100 mL) and sat. $NaHCO_3$ (80 mL). The aqueous layer was back extracted with additional EtOAc (2×40 mL), after which the combined organic phases were washed with brine (100 mL), dried over $Na_2SO_4$, and evaporated to dryness. Crude product was purified with $SiO_2$ chromatography (0-10% MeOH in DCM v/v) to give ring closed bicyclic intermediate (0.59 g, 89%) as a white foam. The bicyclic intermediate (0.715 g, 1.6 mmol) was dissolved in DMF (60 mL) and sodium benzoate added (0.68 g, 4.7 mmol). The solution was heated to 130° C. for 5 h and then allowed to cool to room temperature overnight. Solid material was removed by filtration and washed well with DMF. The combined washes were concentrated in vacuo to a brownish solid. The solid material was dissolved in DCM (100 mL) and additional precipitates removed by filtration. The isolated material was purified by silica gel chromatography (2%-5% MeOH in DCM v/v) to give (1R,3R,4R,8S)-1-benzoyloxymethyl-8-benzyloxy-3-(thymin-1-yl)-2,6-dioxabicyclo[3,2,1]octane 10 (0.70 g, 93%) as a white foam. ES/MS (M-H) m/z: 477.

Example 9

Synthesis of (1S,3R,4R,8S)-8-hydroxy-1-(4,4'-dimethoxytrityloxymethyl)-3-(thymin-yl)-2,6-dioxabicyclo[3,2,1]octane To a solution of 10 (0.43 g, 0.9 mmol) in 1:1 THF/water (12 mL) was added 2 M NaOH (3 mL). The turbid solution was allowed to stir at room temperature for 90 minutes after which AcOH (0.5 mL) was added. The resulting mixture was concentrated to a solid in vacuo and purified by silica gel chromatography (5%-10% MeOH/DCM v/v) to give the intermediate (1S,3R,4R,8S)-8-benzyloxyoxy-1-hydroxymethyl-3-(thymin-yl)-2,6-dioxabicyclo[3,2,1]octane (0.29 g, 77%) as a white foam. This material was dissolved in MeOH (8 mL) after which ammonium formate (0.14 g, 2.3 mmol) and $Pd(OH)_2/C$ (0.125 g) were added. The suspension was heated to reflux for 3 h and then allowed to cool to room temperature. The cooled solution was filtered through a bed of celite which was then washed well with additional MeOH (100 mL). The filtrate was concentrated to a foam (0.22 g) and dried. The crude nucleoside was then dissolved in anhydrous pyridine (15 mL) and DMTrCl (0.34 g, 1.0 mmol) was added. The solution was allowed to stir overnight under a nitrogen atmosphere and then concentrated in vacuo to a viscous material that was partitioned between EtOAc (60 mL) and brine (100 mL). The organic layer was washed with additional brine (100 mL) and then dried over $Na_2SO_4$. The crude product was purified by silica gel chromatography (5%-10% gradient of MeOH/DCM v/v) to give (1S,3R,4R,8S)-8-hydroxy-1-(4,4'-dimethoxytrityloxymethyl)-3-(thymin-yl)-2,6-dioxabicyclo[3,2,1]octane 11 (0.4 g, 88%) as a white foam. ES/MS (M-H) m/z: 585.

Example 10

Synthesis of (1S,3R,4R,8S)-8-hydroxy-1-(4,4'-dimethoxytrityloxymethyl)-3-(thymin-yl)-2,6-dioxabicyclo[3,2,1]octane In an alternative embodiment, (1S,3R,4R,8S)-8-hydroxy-1-(4,4'-dimethoxytrityloxymethyl)-3-(thymin-yl)-2,6-dioxabicyclo[3,2,1]octane 11 can be prepared as follows,

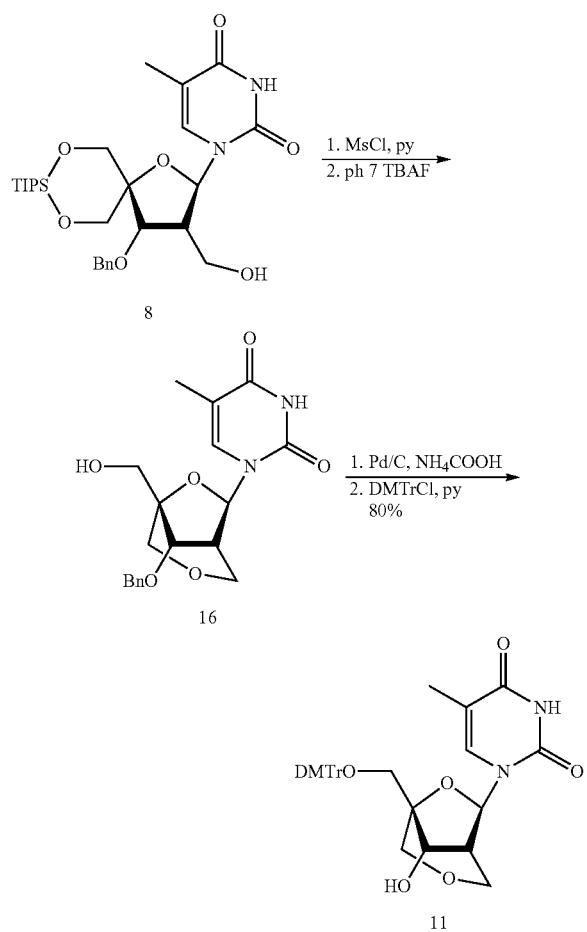

This route to (1S,3R,4R,8S)-8-hydroxy-1-(4,4'-dimethoxytrityloxymethyl)-3-(thymin-yl)-2,6-dioxabicyclo[3,2,1]octane 11 can be achieved by performing a reverse ring closure whereby the displaced mesylate is installed at the 2'-position rather than the 4' as described above. Compound 8 is mesylated at the 2'-hydroxymethyl using standard conditions. The TIPS group is then removed using buffered TBAF, and thereafter sodium hydroxide is added directly to the reaction mixture. Upon heating, the 2' mesylate is smoothly displaced by the 4'-hydroxymethyl group to afford compound 16 in good yields. This material can now easily be converted directly to compound 11 by hydrogenation followed by tritylation. This route increases greatly the yields of 11.

Example 11

(1S,3R,4R,8S)-8-benzyloxyoxy-1-hydroxymethyl-3-(thymin-yl)-2,6-dioxabicyclo[3,2,1]octane To a solution of 8 (1.0 g, 1.58 mmol) in anhydrous pyridine (30 mL) was added mesylchloride (0.16 mL, 2.05 mmol) dropwise. The reaction was stirred at room temperature under a bed of nitrogen for 3 h. The reaction was quenched by addition of MeOH (2 mL) and then concentrated to dryness. The resulting crude material was partitioned between EtOAc (80 mL) and sat NaHCO$_3$ (80 mL). The aqueous phase was extracted with additional EtOAc (60 mL) and the combined organic phases were washed with water (80 mL), brine (80 mL) and then dried (Na$_2$SO$_4$) and concentrated in vacuo. Purification by SiO$_2$ (20%-80% EtOAc/Hexanes) gave 0.94 grms of the intermediate mesylate 84%. This material was dissolved in 19 ml of 0.5M buffered TBAF (1M HOAc) and stirred at room temperature for 30 min. 2 M sodium hydroxide (9 mL) was then added to the reaction which was then heated to 60° C. for 90 min. The reaction was cooled to room temperature and then concentrated to dryness. The residue was suspended in MeOH (20 mL) and dried down on SiO$_2$ (12 g). Purification (0-10% MeOH/DCM) gave (1S,3R,4R,8S)-8-benzyloxyoxy-1-hydroxymethyl-3-(thymin-yl)-2,6-dioxabicyclo[3,2,1]octane 16 (0.35 g, 71%) as a white foam.

Example 12

Synthesis of (1S,3R,4R,8S)-1-(4,4'-dimethoxytrityloxymethyl)-3-(thymin-yl)-2,6-dioxabicyclo[3,2,1]octane 8-O-(2 cyanoethyl-N,N-diisopropylphosphoroamidite Compound 11 (0.48 g, 0.82 mmol) was dissolved in anhydrous DCM (40 mL) at room temperature under nitrogen and diisopropylethyl amine (0.86 mL, 4.91 mmol) was added followed by dropwise addition of 2-cyanoethyl-N,N'-diisopropylchlorophosphoramidite (0.55 mL, 2.46 mmol). After stirring for 6 h the reaction mixture was diluted with EtOAc (100 mL) and washed with sat. NaHCO$_3$ (80 mL). The aqueous phase was back-extracted with EtOAc (100 mL), and the combined organic phases were washed with brine (150 mL), dried (Na$_2$SO$_4$) and concentrated. Crude product was purified using SiO$_2$ column chromatography (gradient of 66% Hex/EtOAc v/v with 0.5% of TEA to 66% EtOAc/Hexanes v/v with 0.5% of TEA) to give (1S,3R,4R,8S)-1-(4,4'-dimethoxytrityloxymethyl)-3-(thymin-yl)-2,6-dioxabicyclo[3,2,1]octane 8-O-(2-cyanoethyl-N,N-diisopropylphosphoroamidite 12 (0.496 g, 77%) as a white foam. ES/MS (M-H) m/z: 785.

Example 13

Synthesis of (1S,3R,4R,8S)-8-triethylsilyloxy-1-(4,4'-dimethoxytrityloxymethyl)-3-(N$^4$-thymin-yl)-2,6-dioxabicyclo[3,2,1]octane Compound 11 was dissolved in DMF (5 mL) and imidazole (0.24 g, 3.4 mmol) was added followed by TESCl (0.29 g, 1.7 mmol). The reaction was stirred at room temperature under nitrogen for 5 h. The mixture was then diluted with of EtOAc (50 mL) and washed with sat. NaHCO$_3$ (40 mL). The aqueous phase was back-extracted with EtOAc (50 mL), and the combined organic phases were washed with brine (100 mL), dried (Na$_2$SO$_4$), and concentrated. Crude product was purified using SiO$_2$ column chromatography (0-60% EtOAC/Hexanes v/v) to give (1S,3R,4R,8S)-8-triethylsilyloxy-1-(4,4'-dimethoxytrityloxymethyl)-3-(N$^4$-thymin-yl)-2,6-dioxabicyclo[3,2,1]octane 13 (0.535, 90%) as a colorless oil. ES/MS (M-H) m/z: 699.

Example 14

Synthesis of (1S,3R,4R,8S)-8-triethylsilyloxy-1-(4,4'-dimethoxytrityloxymethyl)-3-(N$^4$-benzoyl-5-methyl cytosin-yl)-2,6-dioxabicyclo[3,2,1]octane An oven dried nitrogen flushed flask was charged with 1,2,4-triazole (1.77 g, 25.6 mmol) and anhydrous acetonitrile (50 mL). After the 1,2,4-triazole dissolved, the reaction mixture was cooled in ice-bath to 0° C. (triazole precipitated). POCl$_3$ (0.53 mL, 5.73 mmol) was added dropwise and stirring was continued for 10 minutes at 0° C. Triethylamine (4.1 mL, 30 mmol) was then added dropwise keeping the bath temperature at 0° C. and the reaction mixture was stirred an additional 30 minutes. Compound 13 (0.53, 0.76 mmol) in acetonitrile (15 mL) was then slowly added dropwise and stirred for 10 min. The reaction mixture was removed from the ice-bath and stirred at room temperature for 4 h under nitrogen atmosphere. The mixture was then concentrated to approximately 50% of its volume, partitioned between sat. NaHCO$_3$ (50 mL) and EtOAc (60 mL). After separation the aqueous phase was back extracted with EtOAc (40 mL), and the combined organic phases were washed with water (100 mL), brine (100 mL), dried over (Na$_2$SO$_4$), and concentrated to an oily residue. The residue was dissolved in dioxane (12.5 mL) and conc. Aqueous ammonia (5 mL) was added. The reaction mixture was stirred for 1 h at room temperature, after which solvent was removed under reduced pressure. The residue was then re-dissolved in acetonitrile (2×65 mL) and co-evaporated to dryness. The dried material was dissolved in DMF (5 mL) and benzoic anhydride (0.26, 1.15 mmol) was added. The reaction mixture was stirred for 21 h at room temperature. The solution was diluted with EtOAc (80 mL) and washed with sat. NaHCO$_3$ (2×60 mL) and brine (60 mL), dried (Na$_2$SO$_4$), and concentrated. The crude product was dissolved in THF (7.6 mL) and TBAF (1M in THF) (1.15 mL, 1.15 mmol) solution was added. After 15 minutes the reaction mixture was diluted with brine (60 mL) and product was extracted with EtOAc (2×50 mL). Crude product was purified by SiO$_2$ column chromatography (0-80% EtOAc/Hexanes v/v) to give (1S,3R,4R,8S)-8-triethylsilyloxy-1-(4,4'-dimethoxytrityloxymethyl)-3-(N$^4$-benzoyl-5-methyl cytosin-yl)-2,6-dioxabicyclo[3,2,1]octane 14 (0.5 g, 94%) as a white foam. ES/MS (M-H) m/z: 688.

Example 15

Synthesis of (1S,3R,4R,8S)-1-(4,4'-dimethoxytrityloxymethyl)-3-(N$^4$-benzoyl-5-methylcytosin-yl)-2,6-dioxabicyclo[3,2,1]octane 8-O-(2-cyanoethyl-N,N diisopropylphosphoramidite Compound 14 (0.5 g, 0.72 mmol) was dissolved in anhydrous DCM (36 ml) at room temperature under nitrogen and diisopropylethyl amine (0.75 mL, 4.33 mmol) was added followed by dropwise addition of 2-cyanoethyl-N,N'-diisopropylchlorophosphoramidite (0.75 mL, 4.33 mmol). After stirring for 6 h the reaction mixture was diluted with EtOAc (100 mL) and washed with sat. NaHCO$_3$ (80 ml). The aqueous phase was back-extracted with EtOAc (100 mL), and the combined organic phases were washed with brine (150 mL), dried (Na$_2$SO$_4$) and concentrated. Crude product was purified using SiO$_2$ column chromatography (gradient of 66% Hex/EtOAc v/v with 0.5% of TEA to 66% EtOAc/Hexanes v/v with 0.5% of TEA) to give (1S,3R,4R,8S)-1-(4,4'-dimethoxytrityloxymethyl)-3-(N$^4$-benzoyl-5-methylcytosin-yl)-2,6-dioxabicyclo[3,2,1] octane 8-O-(2-cyanoethyl-N,N-diisopropylphosphoramidite 15 (0.48 g, 75%) as a white foam. ES/MS (M-H) m/z: 889.

Example 16

RNA Targeting Survivin (BIRC5)

Sequence specific RNAs targeting Survivin (BIRC5) are shown in Tables 1 and 2. CRN monomers in the sequences of Tables 1 and 2 are identified as "crnX" where X is the one letter code for the nucleotide: A, U, C or G. For example, "crnC" indicates a cytidine CRN. The CRN in Tables 1 and 2 is based on Monomer R. Each one of sense sequences SEQ ID NOs:1-10 will complex with one of the antisense sequences SEQ ID NOs:11-20, respectively, in other words, SEQ ID NO:1 will complex with SEQ ID NO:11, SEQ ID NO:2 will complex with SEQ ID NO:12, and so forth.

TABLE 1

RNA Targeting Survivin

| SEQ ID NO: | Sense Sequence (5' to 3' left to right) |
|---|---|
| 1 | CUGCCUGGCAGCCCUUUCcrnU |
| 2 | CcrnUGCCUGGCAGCCCUUUCUUcrnU |
| 3 | crnUcrnCUGCCUGGCAGCCCUUUCUUcrnU |
| 4 | CcrnUcrnGCCUGGCAGCCCUUUCUUcrnU |
| 5 | CUGCCUGGCAGCCCUUUCcrnUUU |
| 6 | CcrnUGCCUGGCAGCCCUUUCcrnUUU |
| 7 | crnCcrnUGCCUGGCAGCCCUUUCcrnUUU |
| 8 | UcrnCcrnUGCCUGGCAGCCCUUUCcrnUUU |
| 9 | GACCACCGCAUCUCUAcrnCAcrnU |
| 10 | GcrnACCACCGCAUCUCUACAcrnUUcrnU |

TABLE 2

RNA Targeting Survivin

| SEQ ID NO: | Antisense Sequence (5' to 3') |
|---|---|
| 11 | AGAAAGGGCUGCCAGGCAG |
| 12 | AGAAAGGGCUGCCAGGCAGUU |
| 13 | AGAAAGGGCUGCCAGGCAGUU |
| 14 | AGAAAGGGCUGCCAGGCAGUU |
| 15 | AGAAAGGGCUGCCAGGCAGUU |
| 16 | AGAAAGGGCUGCCAGGCAGUU |
| 17 | AGAAAGGGCUGCCAGGCAGUU |
| 18 | AGAAAGGGCUGCCAGGCAGUU |
| 19 | AUGUAGAGAUGCGGUGGUC |
| 20 | AUGUAGAGAUGCGGUGGUCUU |

Example 17

RNA Targeting PLK

Sequence specific RNAs targeting PLK1 are shown in Tables 3 and 4. CRN monomers in the sequences of Tables 3 and 4 are identified as "crnX" where X is the one letter code for the nucleobase: A, U, C or G. For example, "crnC" indicates a cytosine CRN. The CRN in Tables 3 and 4 is based on Monomer R. Each one of sense sequences SEQ ID NOs:21-30 will complex with one of the antisense sequences SEQ ID NOs:31-40, respectively, SEQ ID NO:21 will complex with SEQ ID NO:31, SEQ ID NO:22 will complex with SEQ ID NO:32, and so forth. "d" refers to "deoxy."

TABLE 3

RNA Targeting PLK1

| SEQ ID NO: | Sense Sequence (5' to 3') |
|---|---|
| 21 | GAGGUCCUAGUGGACCCACGCAcrnGCC |
| 22 | AcrnGGUCCUAGUGGACCCACGCAGCCcrnG |
| 23 | crnCcrnCUAGUGGACCCACGCAGCCGGcrnCGcrnG |
| 24 | GcrnUcrnGGACCCACGCAGCCGGCGGCcrnCcrnU |
| 25 | CUCCUGGAGCUGCACAAGAGGAGcrnGcrnA |
| 26 | CCcrnUGGAGCUGCACAAGAGGAGGAcrnAA |
| 27 | crnGGCUGCCAGUACCUGCACCGAAcrnAcrnCC |
| 28 | GACCUCAAGCUGGGCAACCUUUUcrnCcrnC |
| 29 | GCCUAAAAGAGACCUACCUCCGGAU |
| 30 | ACCUACCUCCGGAUCAAGAAGAAUG |

TABLE 4

RNA Targeting PLK1

| SEQ ID NO: | Antisense Sequence (5' to 3') |
|---|---|
| 31 | GGCUGCGUGGGUCCACUAGGACCUCCG |
| 32 | CGGCUGCGUGGGUCCACUAGGACCUCC |
| 33 | CCGCCGGCUGCGUGGGUCCACUAGGAC |
| 34 | AGCGCCGCCGGCUGCGUGGGUCCACUA |
| 35 | UCCUCCUCUUGUGCAGCUCCAGGAGAG |
| 36 | UUUCCUCCUCUUGUGCAGCUCCAGGAG |
| 37 | GGUUUCGGUGCAGGUACUGGCAGCCAA |
| 38 | GGAAAAGGUUGCCCAGCUUGAGGUCUC |
| 39 | AUCCGGAGGUAGGUCUCUUUUAGGcrnCAA |
| 40 | CcrnAUUCUUCUUGAUCCGGAGGUAGGUCcrnU |

Example 18

RNA Targeting Factor VII

Sequence specific RNAs targeting Factor VII are shown in Tables 5 and 6. The CRN in Tables 5 and 6 is based on Monomer R. Each one of sense sequences SEQ ID NOs: 41-50 will complex with one of the antisense sequences SEQ ID NOs:51-60, respectively, in other words, SEQ ID NO:41 will complex with SEQ ID NO:51, SEQ ID NO:42 will complex with SEQ ID NO:52, and so forth. The designation "unaU" refers to an hydroxymethyl substituted nucleomonomer (unlocked nucleomonomer, UNA) having a U nucleobase. The designation "mU" refers to modified nucleotide "um" which is 2'-O-methyluridine.

TABLE 5

RNA Targeting Factor VII

| SEQ ID NO: | Sense Sequence (5' to 3') |
|---|---|
| 41 | CCAUGUGGAAAAAUACCUAcrnUmU |
| 42 | CUGGAUUUCUUACAGUGAUmUcrnU |
| 43 | AGUGGCUGCAAAAGCUCAUcrnUcrnU |
| 44 | crnGGCAGGUCCUGUUGUUGGUmUmU |
| 45 | CcrnCAGGGUCUCCCAGUACAUmUmU |
| 46 | crnUcrnCGAGUGGCUGCAAAAGCUmUmU |
| 47 | crnGCcrnGGCUGUGAGCAGUACUGmUmU |
| 48 | crnAGGAUGAcrnCCAGCUGAUCUGmUmU |
| 49 | crnCGAUGCUGACUCCAUGUGUmUmU |
| 50 | crnGGCGGUUGUUUAGCUCUCAmUmU |

TABLE 6

RNA Targeting Factor VII

| SEQ ID NO: | Antisense Sequence (5' to 3') |
|---|---|
| 51 | UAGGUAUUUUUCCACAUGGmUmU |
| 52 | AUCACUGUAAGAAAUCCAGmUmU |
| 53 | AUGAGCUUUUGCAGCCACUmUmU |
| 54 | ACCAACAACAGGACCUGCCmUmU |
| 55 | AUGUACUGGGAGACCCUGGmUmU |
| 56 | AGCUUUUGCAGCCACUCGAmUmU |
| 57 | CAGUACUGCUCACAGCCGCCmUmU |
| 58 | CAGAUCAGCUGGUCAUCCUmUmU |
| 59 | ACACAUGGAGUCAGCAUCGmUmU |
| 60 | UGAGAGCUAAACAACCGCCmUmU |

Example 19

RNA Targeting ApoB

Sequence specific RNAs targeting ApoB are shown in Tables 7 and 8. The CRN in Tables 7 and 8 is based on Monomer R. Each one of sense sequences SEQ ID NOs: 61-66 will complex with one of the antisense sequences SEQ ID NOs:67-72, respectively, in other words, SEQ ID NO:61 will complex with SEQ ID NO:67, SEQ ID NO:62 will complex with SEQ ID NO:68, and so forth.

TABLE 7

RNA Targeting ApoB

| SEQ ID NO: | Sense Sequence (5' to 3') |
|---|---|
| 61 | GGACAUUCAGAACAAGAAAUcrnU |
| 62 | ACAGAGUCCCUCAAACAGAcrnUU |
| 63 | CAUCACACUGAAUACCAAUcrnUcrnU |

TABLE 7 -continued

RNA Targeting ApoB

| SEQ ID NO: | Sense Sequence (5' to 3') |
|---|---|
| 64 | AAGGGAAUCUUAUAUUUGAUCCAcrnAcrnA |
| 65 | crnACAGAGUCCCUCAAACAGACAUGAC |
| 66 | GcrnUCUCAAAAGGUUUACUAAUAUUCcrnG |

TABLE 8

RNA Targeting ApoB

| SEQ ID NO: | Antisense Sequence (5' to 3') |
|---|---|
| 67 | UUUCUUGUUCUGAAUGUCCUU |
| 68 | UCUGUUUGAGGGACUCUGUUU |
| 69 | AUUGGUAUUCAGUGUGAUGUU |
| 70 | UUUGGAUCAAAUAUAAGAUUCCCUUCU |
| 71 | GUCAUGUCUGUUUGAGGGACUCUGUGA |
| 72 | CGAAUAUUAGUAAACCUUUUGAGACUG |

Example 20

CRN-Antimir-122-8a

The CRN-containing antimir CRN-Antimir-122-8a was synthesized by the methods of this invention. MicroRNA-122 is an miRNA shown to be liver-specific and involved in lipid metabolism and possibly hepatitis C virus replication. MicroRNA-122 regulates various downstream mRNAs. CRN-Antimir-122-8a is 16-mer oligonucleotide complementary to the 5' end of microRNA-122 that can silence microRNA-122 and de-repress its downstream targets.

The structure of CRN-Antimir-122-8a is as follows:

(SEQ ID NO: 73)
crnm5CsdCsdAscrnTscrnTsdGscrnTscrnm5CsdAscrnm5Csd
AsdCsdTscrnm5Cscrnm5CsdA where "crn" preceding a nucleotide code designates a CRN based on Monomer R where X is O, "s" represents a phosphorthioate linkage, the designation crnm5C means a CRN based on Monomer R where X is O and base 5-methylcytidine (m5C), and "d" preceding a nucleotide code designates a deoxy nucleotide.

Example 21

Efficacy of CRN-Containing Antimir CRN-Antimir-122-8a in De-Repression of Mouse mRNA CRN-substituted Antimir-122 demonstrated de-repression of downstream genes ALDOA, SLC7A, P4H4 in the mouse model.

The CRN-containing antimir CRN-Antimir-122-8a was tested in 8-week old BALB/c mice. Treatment groups (n=5) were injected intravenously at a 10 mg/kg dose with a dosing schedule of Q1dx3 (every day for three consecutive days). Necropsy was performed at 24 h after the last dose. Body weights and clinical signs were monitored during the course of the study. Liver and spleen were harvested. CRN-substituted Antimir-122 was well tolerated. Spleen weights of the CRN-Antimir-122-8a treated animals were found to be unaltered relative to the buffer control indicating no non-specific immune response to the CRN substituted Antimir.

The end points determined were expression of downstream genes AldoA (Aldolase A), P4H4 (Prolyl 4-hydroxylase gene), and SLC7A1 (Solute carrier family 7). Negative control was a mismatched Antimir-122 sequence.

Up to 2.5-fold de-repression in liver AldoA mRNA was observed with CRN substituted Antimir-122 relative to buffer control. Under the same conditions, no effect was observed with negative control compared to buffer.

Up to 1.5-fold de-repression in liver P4H4 mRNA was observed with CRN substituted Antimir-122 relative to buffer control. Under the same conditions, no effect was observed with negative control compared to buffer.

Up to 1.3-fold de-repression in liver SLC7A1 mRNA was observed with CRN substituted Antimir-122 relative to buffer control. Under the same conditions, no effect was observed with negative control compared to buffer.

No body weight loss was observed after dosing with CRN-substituted Antimir-122. No alterations in liver and kidney enzymes were observed in CRN treated mice. Other serum chemistry parameters were within expected normal levels.

---

What is claimed is:

1. A method for making a compound having Formula V

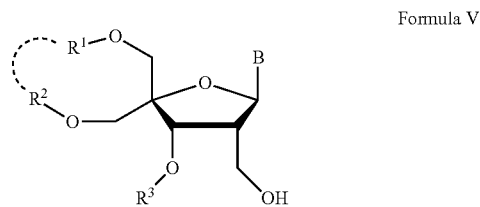

Formula V wherein $R^1$ is a substituent protecting group, $R^2$ is a substituent protecting group, one or both of $R^1$ and $R^2$ are bulky substituent protecting groups, $R^1$ and $R^2$ are optionally linked, $R^3$ is a protecting group, and B is a nucleobase or nucleobase analog, the method comprising providing a compound having Formula II,

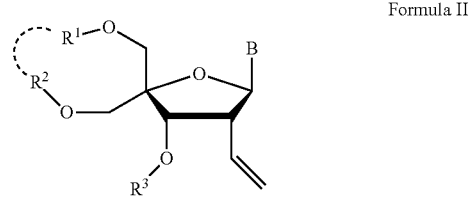

Formula II transforming the compound having Formula II by ozonolysis or oxidation, followed by contacting with a reducing agent, and isolating the compound having Formula V, wherein the bulky substituent protecting groups are selected from trimethylsilyl (TMS), tert-butyldimethylsilyl (TB-DMS), tri-iso-propylsilyloxymethyl (TOM) and dimethoxytrityl (DMT).

2. The method of claim 1, wherein B is 1-uracilyl or 5-methyl-1-uracilyl.

3. The method of claim 1, wherein $R^1$ and $R^2$, optionally linked, is a 1,1,3,3-tetraalkyldisiloxane-1,3-diyl group.

4. The method of claim 1, wherein $R^1$ and $R^2$, optionally linked, is a 1,1,3,3-tetraisopropyldisiloxane-1,3-diyl group.

5. The method of claim 1, wherein $R^3$ is benzyl.

6. The method of claim 1, wherein the yield of the compound having Formula V by ozonolysis is at least 50% at a scale of at least 5 grams of the compound having Formula V.

7. The method of claim 1, wherein the yield of the compound having Formula V by ozonolysis is at least 50% at a scale of at least 10 grams of the compound having Formula V.

8. The method of claim 1, wherein the yield of the compound having Formula V ozonolysis is at least 70% at a scale of at least 10 grams of the compound having Formula V.

9. The method of claim 1, wherein the yield of the compound having Formula V ozonolysis is at least 80% at a scale of at least 10 grams of the compound having Formula V.

10. The method of claim 1, further comprising transforming the compound having Formula V to a conformationally restricted nucleomonomer CRN having Formula VI,

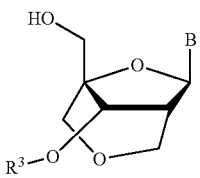

Formula VI by the steps of:
deprotecting the 4'-hydroxymethyl groups of Formula V; and
forming a 2'-4' —CH₂OCH₂— bridge.

11. The method of claim 10, wherein the conformationally restricted nucleomonomer is a pyrimidine CRN.

12. A compound having the structure

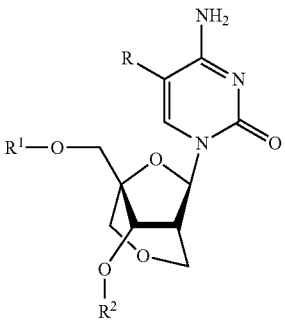

wherein R is methyl, $R^1$ is independently H, alkyl, or a protecting group, and $R^2$ is independently H, alkyl, a protecting group, or a phosphoramidityl group.

13. A nucleic acid compound comprising a residue of the compound of claim 12.

14. The nucleic acid compound of claim 13, wherein the nucleic acid compound is a single stranded oligonucleotide or a double-stranded oligonucleotide.

15. The nucleic acid compound of claim 13, wherein the nucleic acid compound is a microRNA, an antimir, an antagomir, a microRNA mimetic, a microRNA precursor, an RNA, a short interfering RNA or siRNA, a DNA, an RNA and DNA, a meroduplex RNA or mdRNA, a short hairpin RNA or shRNA, or an antisense oligonucleotide.

16. A compound having the structure

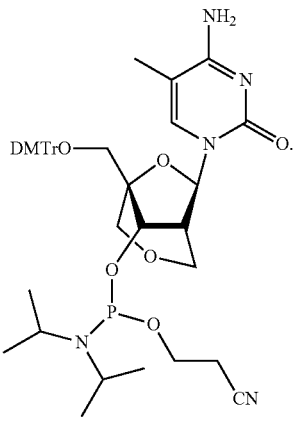

17. A nucleic acid compound comprising a residue of the compound of claim 16.

18. The nucleic acid compound of claim 17, wherein the nucleic acid compound is a single stranded oligonucleotide or a double-stranded oligonucleotide.

19. The nucleic acid compound of claim 17, wherein the nucleic acid compound is a microRNA, an antimir, an antagomir, a microRNA mimetic, a microRNA precursor, an RNA, a short interfering RNA or siRNA, a DNA, an RNA and DNA, a meroduplex RNA or mdRNA, a short hairpin RNA or shRNA, or an antisense oligonucleotide.

\* \* \* \* \*